United States Patent
Cohen et al.

(10) Patent No.: US 7,345,081 B2
(45) Date of Patent: Mar. 18, 2008

(54) AZABICYCLO-OCTANE INHIBITORS OF IAP

(75) Inventors: Frederick Cohen, San Francisco, CA (US); Wayne Fairbrother, Burlingame, CA (US); John Flygare, Burlingame, CA (US); Stephen Franz Keteltas, San Francisco, CA (US); Vickie Hsiao-Wei Tsui, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 557 days.

(21) Appl. No.: 11/088,008

(22) Filed: Mar. 22, 2005

(65) Prior Publication Data

US 2005/0261203 A1 Nov. 24, 2005

Related U.S. Application Data

(60) Provisional application No. 60/555,755, filed on Mar. 23, 2004.

(51) Int. Cl.
*A61K 31/403* (2006.01)
*C07D 209/02* (2006.01)

(52) U.S. Cl. ............... 514/414; 548/452; 548/465; 514/412

(58) Field of Classification Search ............... 548/452, 548/465; 514/412, 414
See application file for complete search history.

(56) References Cited

U.S. PATENT DOCUMENTS

| | | | |
|---|---|---|---|
| 4,278,793 | A | 7/1981 | Durckheimer et al. |
| 4,720,484 | A | 1/1988 | Vincent et al. |
| 5,411,942 | A | 5/1995 | Widmer et al. |
| 5,559,209 | A | 9/1996 | Nishimoto |
| 6,472,172 | B1 | 10/2002 | Deng et al. |
| 6,608,026 | B1 | 8/2003 | Wang et al. |
| 6,992,063 | B2 | 1/2006 | Shi |
| 7,041,784 | B2 | 5/2006 | Wang et al. |
| 2002/0177557 | A1 | 11/2002 | Shi |
| 2003/0157522 | A1 | 8/2003 | Boudreault et al. |
| 2006/0052311 | A1 | 3/2006 | Sharma et al. |

FOREIGN PATENT DOCUMENTS

| | | |
|---|---|---|
| WO | WO 92/01938 | 2/1992 |
| WO | WO 00/00823 | 1/2000 |
| WO | WO 00/39585 | 7/2000 |
| WO | WO 02/16402 | 2/2002 |
| WO | WO 02/16418 | 2/2002 |
| WO | WO 02/26775 A2 | 4/2002 |
| WO | WO 02/30959 | 4/2002 |
| WO | WO 02/096930 A2 | 12/2002 |
| WO | WO 03/010184 A2 | 2/2003 |
| WO | WO 03/086470 | 10/2003 |
| WO | WO 2004/005248 A1 | 1/2004 |
| WO | WO 2004/007529 A2 | 1/2004 |
| WO | WO 2004/017991 A1 | 3/2004 |
| WO | WO 2004/072641 | 8/2004 |
| WO | WO 2004/106371 A1 | 12/2004 |
| WO | WO 2005/049853 | 6/2005 |
| WO | WO 2005/097791 A1 | 10/2005 |
| WO | WO 2006/020060 A2 | 2/2006 |

OTHER PUBLICATIONS

U.S. Appl. No. 10/364,645, filed Jul. 2, 2003, Franklin, M. et al.
U.S. Appl. No. 10/983,495, filed Aug. 11, 2004, Fairbrother, W. et al.
Arnt et al., "Synthetic Smac/DIABLO Peptides Enhance the Effects of Chemotherapeutic Agents by Binding XIAP and cIAP1 in Situ" *J. Bio. Chem.* 277(46):44236-44243 (Nov. 2002).
Baktiar, et al., "Transfer of alkoxycarbonyl frpm alkyl imidazolium-2-carboxylates to benzyl alcohol, a cyclohexanone enamine and diethylamine" *J. Chem. Soc. Perkin Trans. 1* 3:329-243 (Jan. 1994).
Blass, B.E. et al., "Parallel Synthesis and Evaluation of N-(1-Phenylethyl)-5-phenyl-imidazole-2-amines as Na+/K+ ATPase inhibitors" *Bioorg. Med. Chem. Lett.* 10:1543-1545 (2000).
Chai et al., "Structural and Biochemical Basis of Apoptotic Activation by Smac/DIABLO" *Nature* 406:855-862 (Aug. 2000).
Corey, E.J. et al., "(+)-1(S), 5(R), 8(S)-phenyl-2-azabicyclo [3.3.0]OCTAN-8-0L N, O-methylboronate (2) and its enantiomer, chiral chemzymes which serve as catalysts_for their own enantioselective synthesis" *Tetrahedron Letters* 30(41):5547-5550 (1989).

(Continued)

*Primary Examiner*—Golam M. M. Shameem
(74) *Attorney, Agent, or Firm*—David W Evans

(57) ABSTRACT

The invention provides novel inhibitors of IAP that are useful as a therapeutic agents for treating malignancies where the compounds have the general formula I:

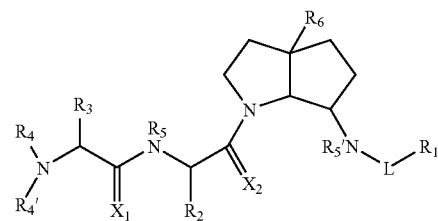

$X_1$ and $X_2$ are independently O or S; L is a bond or —C($X_3$)—, —C($X_3$)N$R_{12}$, —C($X_3$)O— wherein $X_3$ is O or S and $R_{12}$ is H or $R_1$; $R_1$ is alkyl, a carbocycle, carbocycle-substituted alkyl, a heterocycle or heterocycle-substituted alkyl, wherein each is optionally substituted with halogen, hydroxyl, mercapto, carboxyl, alkyl, haloalkyl, alkoxy, alkylsulfonyl, amino, nitro, aryl and heteroaryl; $R_2$ is alkyl, cycloalkyl, cycloalkylalkyl, aryl, aralkyl, a heterocycle or heterocyclylalkyl; $R_3$ is H or alkyl; $R_4$ and $R_{4'}$ are independently H, alkyl, aryl, aralkyl, cycloalkyl, cycloalkylalkyl, heteroaryl, or heteroaralkyl wherein each is optionally substituted with halogen, hydroxyl, mercapto, carboxyl, alkyl, alkoxy, amino and nitro; $R_5$, and $R_{5'}$ are each independently H or alkyl; $R_6$ is H or alkyl; and salts and solvates thereof.

20 Claims, No Drawings

OTHER PUBLICATIONS

Crook et al., "An Apoptosis-Inhibiting Baculovirus Gene with a Zinc Finger-Like Motif" *Journal of Virology* 67(4):2168-2174 (Apr. 1993).

Deveraux et al., "Endogenous Inhibitors of Caspases" *J. Clin. Immuno.* 19(6):388-398 (1999).

Deveraux et al., "IAPs Block Apoptotic Events Induced by Caspase-8 and Cytochrome c by Direct Inhibition of Distinct Caspases" *EMBO Journal* 17(8):2215-2223 (1998).

Fong et al., "Expression and genetic analysis of XIAP-associated factor 1 (XAF1) in cancer cell lines" *Genomics* 70:113-122 (2000).

Fulda et al., "Smac Agonists Sensitize for Apo2L/TRAIL- or Anticancer Drug-Induced Apoptosis and Induce Regression of Malignant Glioma in Vivo" *Nature Medicine* 8(8):808-815 (Aug. 2002).

Guo et al., "Ectopic Overexpression of Second Mitochondria-Derived Activator of Caspases (Smac/DIABLO) or Cotreatment with N-Terminus of Smac/DIABLO Peptide Potentiates Epothilone B Derivative- (BMS 247550) and Apo-2L/TRAIL Induced Apoptosis" *Blood* 99:3419-3426 (2002).

Hinds et al., "Solution Structure of a Baculoviral Inhibitor of Apoptosis (IAP) Repeat" *Nat. Struct. Biol.* 6:648-651 (Jul. 1999).

Hu et al., "Antisense oligonucleotides targeting XIAP induce apoptosis and enhance chemotherapeutic activity against human lung cancer cells in vitro and in vivo" *Clin. Cancer Res* 9(7):2826-2836 (2003).

Keating, S.M. et al. *Proceedings of SPIE: In Vito Diagnostic Instrumentation*, Cohn ,G. E., Bellingham, WA pp. 128-137 (2000).

Kolb et al., "Use of a novel homogeneous fluorescent technology in high throughput screening" *J Biomolecular Screening* 1(4):203-210 (1996).

LaCase et al., "The inhibitors of apoptosis (IAPs) and their emerging role in cancer" *Oncogene* 17(25):3247-3259 (1998).

Lin et al., "Resistance of bone marrow-derived macrophages to apoptosis is associated with the expression of X-linked inhibitor of apoptosis protein in primary cultures of bone marrow cells" *Biochemical Journal* 353:299-306 (2001).

Liston et al., "Suppression of apoptosis in mammalian cells by NAIP and a related family of IAP genes" *Nature* 379:349-353 (1996).

Liu et al., "Structural Basis for Binding of Smac/DIABLO to the XIAP BIR3 Domain" *Nature* 408:1004-1008 (Dec. 2000).

Masuda et al., "Studies on mesoinic compounds. Part 11. Alkylation of 5-acylamino-1,2,3-thiadiazoles" *J. Chem. Soc. Perkin. Trans. 1* 5:1591-1595 (1981).

Sasaki et al., "Down-regulation of X-linked inhibitor of apoptosis protein induces apoptosis in chemoresistant human ovarian cancer cells" *Cancer Research* 60(20):5659-5666 (2000).

Tamm et al., "Expression and prognostic significance of IAP-family genes in human cancers and myeloid leukemias" *Clin. Cancer Res.* 6(5):1796-1803 (2000).

Thompson, "Apoptosis in the Pathogenesis and Treatment of Disease" *Science* 267:1456-1462 (1995).

Vucic et al., "ML-IAP, A Novel Inhibitor of Apoptosis that is Preferentially Expressed in Human Melanomas" *Current Bio.* 10:1359-1366 (Oct. 2000).

Vucic et al., "SMAC Negatively Regulates the Anti-apoptotic Activity of Melanoma Inhibitor of Apoptosis (ML-IAP)" *The Journal of Biological Chemistry* 277:12275-12279 (2002).

Wu et al., "Structural Basis of IAP Recognition by Smac/DIABLO" *Nature* 408:1008-1012 (Dec 2000).

Yang et al., "Predominant suppression of apoptosome by inhibitor of apoptosis protein in non-small cell lung cancer H460 cells: therapeutic effect of a novel polyarginine-conjugated smac peptide" *Cancer Research* 63(4):831-837 (2003).

SEQUENCE LISTING

```
<160> NUMBER OF SEQ ID NOS: 1

<210> SEQ ID NO 1
<211> LENGTH: 133
<212> TYPE: PRT
<213> ORGANISM: Homo sapiens

<400> SEQUENCE: 1

Met Gly Ser Ser His His His His His His Ser Ser Gly Leu Val
 1               5                  10                  15

Pro Arg Gly Ser His Met Leu Glu Thr Glu Glu Glu Glu Glu
                20                  25                  30

Gly Ala Gly Ala Thr Leu Ser Arg Gly Pro Ala Phe Pro Gly Met
                35                  40                  45

Gly Ser Glu Glu Leu Arg Leu Ala Ser Phe Tyr Asp Trp Pro Leu
                50                  55                  60
```

-continued

| | | | | | | | | | | | |
|---|---|---|---|---|---|---|---|---|---|---|---|
| Thr | Ala | Glu | Val | Pro | Pro | Glu | Leu | Leu | Ala | Ala | Ala | Gly | Phe | Phe |
| | | | | 65 | | | | 70 | | | | | | 75 |
| His | Thr | Gly | His | Gln | Asp | Lys | Val | Arg | Cys | Phe | Phe | Cys | Tyr | Gly |
| | | | | 80 | | | | | 85 | | | | | 90 |
| Gly | Leu | Gln | Ser | Trp | Lys | Arg | Gly | Asp | Asp | Pro | Trp | Thr | Glu | His |
| | | | | 95 | | | | | 100 | | | | | 105 |
| Ala | Lys | Trp | Phe | Pro | Gly | Cys | Gln | Phe | Leu | Leu | Arg | Ser | Lys | Gly |
| | | | | 110 | | | | | 115 | | | | | 120 |
| Gln | Glu | Tyr | Ile | Asn | Asn | Ile | His | Leu | Thr | His | Ser | Leu |
| | | | | 125 | | | | | 130 |

AZABICYCLO-OCTANE INHIBITORS OF IAP

FIELD OF THE INVENTION

The present invention relates to organic compounds useful for therapy and/or prophylaxis in a mammal, and in particular to azabicyclo-octane inhibitors of IAP proteins useful for treating cancers.

BACKGROUND OF THE INVENTION

Apoptosis or programmed cell death is a genetically and biochemically regulated mechanism that plays an important role in development and homeostasis in invertebrates as well as vertebrates. Aberrancies in apoptosis that lead to premature cell death have been linked to a variety of developmental disorders. Deficiencies in apoptosis that result in the lack of cell death have been linked to cancer and chronic viral infections (Thompson et al., (1995) Science 267, 1456-1462).

One of the key effector molecules in apoptosis are the caspases (cysteine containing aspartate specific proteases). Caspases are strong proteases, cleaving after aspartic acid residues and once activated, digest vital cell proteins from within the cell. Since caspases are such strong proteases, tight control of this family of proteins is necessary to prevent premature cell death. In general, caspases are synthesized as largely inactive zymogens that require proteolytic processing in order to be active. This proteolytic processing is only one of the ways in which caspases are regulated. The second mechanism is through a family of proteins that bind and inhibit caspases.

A family of molecules that inhibit caspases are the Inhibitors of Apoptosis (IAP) (Deveraux et al., J Clin Immunol (1999), 19:388-398). IAPs were originally discovered in baculovirus by their functional ability to substitute for P35 protein, an anti-apoptotic gene (Crook et al. (1993) J Virology 67, 2168-2174). IAPs have been described in organisms ranging from Drosophila to human. Regardless of their origin, structurally, IAPs comprise one to three Baculovirus IAP repeat (BIR) domains, and most of them also possess a carboxyl-terminal RING finger motif. The BIR domain itself is a zinc binding domain of about 70 residues comprising 4 alpha-helices and 3 beta strands, with cysteine and histidine residues that coordinate the zinc ion (Hinds et al., (1999) Nat. Struct. Biol. 6, 648-651). It is the BIR domain that is believed to cause the anti-apoptotic effect by inhibiting the caspases and thus inhibiting apoptosis. As an example, human X-chromosome linked IAP (XIAP) inhibits caspase 3, caspase 7 and the Apaf-1-cytochrome C mediated activation of caspase 9 (Deveraux et al., (1998) EMBO J. 17, 2215-2223). Caspases 3 and 7 are inhibited by the BIR2 domain of XIAP, while the BIR3 domain of XIAP is responsible for the inhibition of caspase 9 activity. XIAP is expressed ubiquitously in most adult and fetal tissues (Liston et al, Nature, 1996, 379(6563):349), and is overexpressed in a number of tumor cell lines of the NCI 60 cell line panel (Fong et al, Genomics, 2000, 70:113; Tamm et al, Clin. Cancer Res. 2000, 6(5):1796). Overexpression of XIAP in tumor cells has been demonstrated to confer protection against a variety of pro-apoptotic stimuli and promotes resistance to chemotherapy (LaCasse et al, Oncogene, 1998, 17(25):3247). Consistent with this, a strong correlation between XIAP protein levels and survival has been demonstrated for patients with acute myelogenous leukemia (Tamm et al, supra). Down-regulation of XIAP expression by antisense oligonucleotides has been shown to sensitize tumor cells to death induced by a wide range of pro-apoptotic agents, both in vitro and in vivo (Sasaki et al, Cancer Res., 2000, 60(20):5659; Lin et al, Biochem J., 2001, 353:299; Hu et al, Clin. Cancer Res., 2003, 9(7):2826). Smac/DIABLO-derived peptides have also been demonstrated to sensitize a number of different tumor cell lines to apoptosis induced by a variety of pro-apoptotic drugs (Arnt et al, J. Biol. Chem., 2002, 277(46):44236; Fulda et al, Nature Med., 2002, 8(8):808; Guo et al, Blood, 2002, 99(9):3419; Vucic et al, J. Biol. Chem., 2002, 277(14):12275; Yang et al, Cancer Res., 2003, 63(4):831).

Melanoma IAP (ML-IAP) is an IAP not detectable in most normal adult tissues but is strongly upregulated in melanoma (Vucic et al., (2000) Current Bio 10:1359-1366). Determination of protein structure demonstrated significant homology of the ML-IAP BIR and RING finger domains to corresponding domains present in human XIAP, C-IAP1 and C-IAP2. The BIR domain of ML-IAP appears to have the most similarities to the BIR2 and BIR3 of XIAP, C-IAP1 and C-IAP2, and appears to be responsible for the inhibition of apoptosis, as determined by deletional analysis. Furthermore, Vucic et al., demonstrated that ML-IAP could inhibit chemotherapeutic agent induced apoptosis. Agents such as adriamycin and 4-tertiary butylphenol (4-TBP) were tested in a cell culture system of melanomas overexpressing ML-IAP and the chemotherapeutic agents were significantly less effective in killing the cells when compared to a normal melanocyte control. The mechanism by which ML-IAP produces an anti-apoptotic activity is through inhibition of caspase 3, 7 and 9. ML-IAP did not effectively inhibit caspases 1, 2, 6, or 8.

Since apoptosis is a strictly controlled pathway with multiple interacting factors, the discovery that IAPs themselves are regulated was not unusual. In the fruit fly *Drosophila*, the Reaper (rpr), Head Involution Defective (hid) and GRIM proteins physically interact with and inhibit the anti-apoptotic activity of the *Drosophila* family of IAPs. In the mammal, the proteins SMAC/DIABLO act to block the IAPs and allow apoptosis to proceed. It was shown that during normal apoptosis, SMAC is processed into an active form and is released from the mitochondria into the cytoplasm where it physically binds to IAPs and prevents the IAP from binding to a caspase. This inhibition of the IAP allows the caspase to remain active and thus proceed with apoptosis. Interestingly, sequence homology between the IAP inhibitors shows that there is a four amino acid motif in the N-terminus of the processed, active proteins. This tetrapeptide appears to bind into a hydrophobic pocket in the BIR domain and disrupts the BIR domain binding to caspases (Chai et al., (2000) Nature 406:855-862, Liu et al., (2000) Nature 408:1004-1008, Wu et al., (2000) Nature 408 1008-1012).

SUMMARY OF THE INVENTION

In one aspect of the present invention there is provided novel inhibitors IAP having the general formula (I)

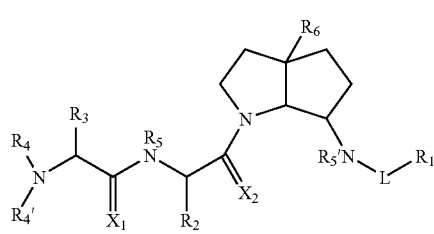

I wherein $X_1$ and $X_2$ are independently O or S;

L is a bond, —C($X_3$)—, —C($X_3$)N$R_{12}$ or —C($X_3$)O— wherein $X_3$ is O or S and $R_{12}$ is H or $R_1$;

$R_1$ is alkyl, a carbocycle, carbocycle-substituted alkyl, a heterocycle or heterocycle-substituted alkyl, wherein each is optionally substituted with halogen, hydroxyl, mercapto, carboxyl, alkyl, haloalkyl, alkoxy, alkylsulfonyl, amino, nitro, aryl and heteroaryl;

$R_2$ is alkyl, cycloalkyl, cycloalkylalkyl, aryl, aralkyl, a heterocycle or heterocyclylalkyl;

$R_3$ is H or alkyl;

$R_4$ and $R_{4'}$ are independently H, alkyl, aryl, aralkyl, cycloalkyl, cycloalkylalkyl, heteroaryl, or heteroaralkyl wherein each is optionally substituted with halogen, hydroxyl, mercapto, carboxyl, alkyl, alkoxy, amino and nitro;

$R_5$ and $R_{5'}$ are each independently H or alkyl;

$R_6$ is H or alkyl;

and salts and solvates thereof.

In another aspect of the invention, there are provided compositions comprising compounds of formula I and a carrier, diluent or excipient.

In another aspect of the invention, there is provided a method of inducing apoptosis in a cell comprising introducing into said cell a compound of formula I.

In another aspect of the invention, there is provided a method of sensitizing a cell to an apoptotic signal comprising introducing into said cell a compound of formula I.

In another aspect of the invention, there is provided a method for inhibiting the binding of an IAP protein to a caspase protein comprising contacting said IAP protein with a compound of formula I.

In another aspect of the invention, there is provided a method for treating a disease or condition associated with the overexpression of an IAP in a mammal, comprising administering to said mammal an effective amount of a compound of formula I.

DETAILED DESCRIPTION OF THE PREFERRED EMBODIMENTS

Definitions

"Alkyl" means a branched or unbranched, saturated or unsaturated (i.e. alkenyl, alkynyl) aliphatic hydrocarbon group, having up to 12 carbon atoms unless otherwise specified. When used as part of another term, for example "alkylamino", the alkyl portion may be a saturated hydrocarbon chain, however also includes unsaturated hydrocarbon carbon chains such as "alkenylamino" and "alkynylamino. Examples of particular alkyl groups include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "$C_1$-$C_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, substituted, alkyl groups may contain one, two, three or four substituents which may be the same or different. Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro (n-butyl), 2-amino(iso-propyl), 2-carbamoyloxyethyl and the like. The alkyl group may also be substituted with a carbocycle group. Examples include cyclopropylmethyl, cyclobutylmethyl, cyclopentylmethyl, and cyclohexylmethyl groups, as well as the corresponding -ethyl, -propyl, -butyl, -pentyl, -hexyl groups, etc. Particular substituted alkyls are substituted methyls e.g. a methyl group substituted by the same substituents as the "substituted $C_n$-$C_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, carboxymethyl, bromomethyl and iodomethyl.

"Amidine" denotes the group —C(NH)—NHR wherein R is H or alkyl or aralkyl. A particular amidine is the group —NH—C(NH)—NH$_2$.

"Amino" denotes primary (i.e. —NH$_2$), secondary (i.e. —NRH) and tertiary (i.e. —NRR) amines. Particular secondary and tertiary amines are alkylamine, dialkylamine, arylamine, diarylamine, aralkylamine and diaralkylamine. Particular secondary and tertiary amines are methylamine, ethylamine, propylamine, isopropylamine, phenylamine, benzylamine dimethylamine, diethylamine, dipropylamine and disopropylamine.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Particular amino protecting groups are Boc, Fmoc and Cbz. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T.W. Greene, "Protective Groups in Organic Synthesis", John Wiley and Sons, New York, N.Y., 1981. The term "protected amino" refers to an amino group substituted with one of the above amino-protecting groups.

"Aryl" when used alone or as part of another term means a carbocyclic aromatic group whether or not fused having the number of carbon atoms designated or if no number is designated, up to 14 carbon atoms. Particular aryl groups include phenyl, naphthyl, biphenyl, phenanthrenyl, naphthacenyl, and the like (see e.g. *Lang's Handbook of Chemistry* (Dean, J. A., ed) $13^{th}$ ed. Table 7-2 [1985]). In a particular embodiment an aryl group is phenyl. Substituted phenyl or substituted aryl denotes a phenyl group or aryl group substituted with one, two, three, four or five substituents chosen, unless otherwise specified, from halogen (F, Cl, Br, I), hydroxy, protected hydroxy, cyano, nitro, alkyl (such as $C_1$-$C_6$ alkyl), alkoxy (such as $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, arylsulfonylamino, heterocyclylsulfonylamino, heterocyclyl, aryl, or other groups specified. One or more methyne (CH) and/or methylene (CH$_2$) groups in these substituents may in turn be substituted with a similar group as those denoted above. Examples of the term "substituted phenyl" includes but is not limited to a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy) phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl,; a mono- or di(hydroxymethyl)phenyl or (protected hydroxymethyl)phenyl such as 3-(protected hydroxymethyl)phenyl or 3,4-di (hydroxymethyl)phenyl; a mono- or di(aminomethyl)phenyl or (protected aminomethyl)phenyl such as 2-(aminomethyl) phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. Particular substituted phenyl groups are 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl) benzyloxy-6-methyl sulfonyl aminophenyl groups. Fused aryl rings may also be substituted with the substituents specified herein, for example with 1, 2 or 3 substituents, in the same manner as substituted alkyl groups.

"Carbocyclyl", "carbocyclylic", "carbocycle" and "carbocyclo" alone and when used as a moiety in a complex group such as a carbocycloalkyl group, refers to a mono-, bi-, or tricyclic aliphatic ring having 3 to 14 carbon atoms, for example 3 to 7 carbon atoms, which may be saturated or unsaturated, aromatic or non-aromatic. Particular saturated carbocyclic groups include cyclopropyl, cyclobutyl, cyclopentyl and cyclohexyl groups. In a particular embodiment saturated carbocyclic groups are cyclopropyl and cyclohexyl. In another particular embodiment a saturated carbocyclic group is cyclohexyl. Particular unsaturated carbocycles are aromatic e.g. aryl groups as previously defined. I particular unsaturated carbocycle is phenyl. The terms "substituted carbocyclyl", "carbocycle" and "carbocyclo" mean these groups substituted by the same substituents as the "substituted alkyl" group.

"Carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl) ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases or reductive conditions employing highly activated metal catalysts such as Raney nickel. (Such harsh removal conditions are also to be avoided when removing amino-protecting groups and hydroxy-protecting groups, discussed below.) Particular carboxylic acid protecting groups are the allyl and p-nitrobenzyl groups. Similar carboxy-protecting groups used in the cephalosporin, penicillin and peptide arts can also be used to protect a carboxy group substituents. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

"Guanidine" denotes the group —NH—C(NH)—NHR wherein R is H or alkyl or aralkyl. A particular guanidine is the group —NH—C(NH)—$NH_2$.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, acetoxy, carbamoyloxy, trifluoro, chloro, carboxy, bromo and iodo groups. Further examples of these groups are found in T. W. Greene and P. G. M. Wuts, "Protective Groups in Organic Synthesis", $2^{nd}$ ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected hydroxy" refers to a hydroxy group substituted with one of the above hydroxy-protecting groups.

"Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated or unsaturated, aromatic (heteroaryl) or non-aromatic ring having the number of atoms designated, generally from 5 to about 14 ring atoms, where the ring atoms are carbon and at least one heteroatom (nitrogen, sulfur or oxygen). In a particular embodiment the group incorporates 1 to 4 heteroatoms. Typically, a 5-membered ring has 0 to 2 double bonds and 6- or 7-membered ring has 0 to 3 double bonds and the nitrogen or sulfur heteroatoms may optionally be oxidized (e.g. SO, $SO_2$), and any nitrogen heteroatom may optionally be quaternized. Particular non-aromatic heterocycles include morpholinyl (morpholino), pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperazinyl and piperidinyl. A "heterocycloalkyl" group is a heterocycle group as defined above covalently bonded to an alkyl group as defined above. Particular 5-membered heterocycles containing a sulfur or oxygen atom and one to three nitrogen atoms include thiazolyl, such as thiazol-2-yl and thiazol-2-yl N-oxide, thiadiazolyl such as 1,3,4-thiadiazol-5-yl and 1,2,4-thiadiazol-5-yl, oxazolyl such as oxazol-2-yl, and oxadiazolyl such as 1,3,4-oxadiazol-5-yl, and 1,2,4-oxadiazol-5-yl. Particular 5-membered ring heterocycles containing 2 to 4 nitrogen atoms include imidazolyl such as imidazol-2-yl; triazolyl such as 1,3,4-triazol-5-yl, 1,2,3-triazol-5-yl, and 1,2,4-triazol-5-yl, and tetrazolyl such as 1H-tetrazol-5-yl. Particular benzo-fused 5-membered heterocycles are benzoxazol-2-yl, benzthiazol-2-yl and benzimidazol-2-yl. Particular 6-membered heterocycles contain one to three nitrogen atoms and optionally a sulfur or oxygen atom, for example pyridyl, such as pyrid-2-yl, pyrid-3-yl, and pyrid-4-yl; pyrimidyl such as pyrimid-2-yl and pyrimid-4-yl; triazinyl such as 1,3,4-triazin-2-yl and 1,3,5-triazin-4-yl; pyridazinyl such as pyridazin-3-yl, and pyrazinyl. Substituents for optionally substituted heterocycles, and further examples of the 5- and 6-membered ring systems discussed above can be found in W. Druckheimer et al., U.S. Pat. No. 4,278,793.

"Heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur (*Lang's Handbook of Chemistry*, supra). Included in the definition are any bicyclic groups where any of the above heteroaryl rings are fused to a benzene ring. The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl. Particularly "heteroaryls" include; 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl. An alternative group of "heteroaryl" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

"Inhibitor" means a compound which reduces or prevents the binding of IAP proteins to caspase proteins or which reduces or prevents the inhibition of apoptosis by an IAP protein.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, trimethamine, dicyclohexylamine, choline, and caffeine.

The present invention provides novel compounds having the general formula I:

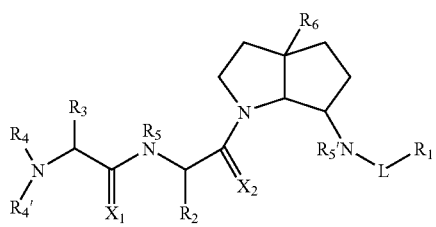

I wherein $X_1$, $X_2$, L, $R_1$, $R_2$, $R_3$, $R_4$, $R_{4'}$, $R_5$, $R_{5'}$ and $R_6$ are as defined herein.

$X_1$ and $X_2$ are each independently O or S. In a particular embodiment, $X_1$ and $X_2$ are both O. In another particular embodiment $X_1$ and $X_2$ are both S. In another particular embodiment, $X_1$ is S while $X_2$ is O. In another particular embodiment, $X_1$ is O while $X_2$ is S.

L is a bond, —C($X_3$)—, —C($X_3$)$NR_{12}$ or —C($X_3$)O— wherein $X_3$ is O or S and $R_{12}$ is H or $R_1$. In a particular embodiment, L is a bond. In another particular embodiment, L is —C($X_3$)— wherein $X_3$ is O. In another particular embodiment, L is —C($X_3$)— wherein $X_3$ is S. In a particular embodiment, L is —C($X_3$)NH— wherein $X_3$ is O. In another particular embodiment, L is —C($X_3$)NH— wherein $X_3$ is S. In a particular embodiment, L is —C($X_3$)O— wherein $X_3$ is O. In another particular embodiment, L is —C($X_3$)O— wherein $X_3$ is S.

$R_1$ is alkyl, a carbocycle, carbocycle-substituted alkyl, a heterocycle or heterocycle-substituted alkyl, wherein each is optionally substituted with halogen, hydroxyl, mercapto, carboxyl, alkyl, haloalkyl, alkoxy, alkylsulfonyl, amino, nitro, aryl and heteroaryl. In a particular embodiment, $R_1$ is alkyl, aryl, aralkyl, cycloalkyl, cycloalkylalkyl, heteroaryl or heteroaralkyl wherein each is optionally substituted with halogen, hydroxyl, mercapto, carboxyl, alkyl, haloalkyl amino, nitro, aryl and heteroaryl. In a particular embodiment $R_1$ is selected from the group consisting of formula IIa, IIb, IIc and IId:

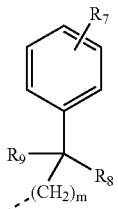

IIa

IIb

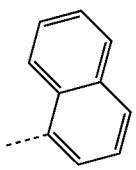

IIc

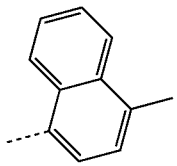

IId wherein $R_7$ is H, alkyl, alkoxy, halogen, hydroxyl, mercapto, carboxyl, amino, nitro, aryl, aryloxy, aralkyl, cycloalkyl, cycloalkylalkyl, heteroaryl, or heteroaralkyl; $R_8$ is H, alkyl, aryl or heteroaryl optionally substituted with halogen, hydroxyl, alkoxy, carboxyl, or amino; $R_9$ is H or alkyl; Y is NH, $NR_{10}$, O or S wherein $R_{10}$ is H, alkyl or aryl; Z is CH, $CH_2$ or N; and m is 0, 1, 2 or 3. In a particular embodiment, $R_1$ is selected from the group consisting of formula IIa, IIb, IIc and IId while L is —C($X_3$)— and in particular when $X_3$ is O.

When $R_1$ is the group of formula IIa, $R_7$ is may be H, halogen, hydroxyl or alkoxy. In a particular embodiment $R_7$ is H, methyl, F or methoxy. In another particular embodiment, $R_1$ is selected from the group consisting of $IIa^1$, $IIa^2$, $IIa^3$ and $IIa^4$:

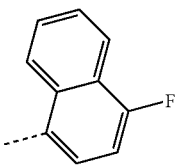

$IIa^1$

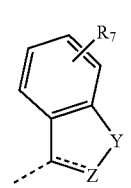

$IIa^2$ $IIa^3$

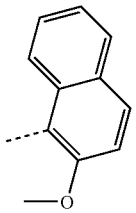

In a particular embodiment, $R_1$ is selected from the group consisting of $IIa^1$, $IIa^2$, $IIa^3$ and $IIa^4$ while L is —$C(X_3)$—. In a particular embodiment $R_1$ is the group of formula $IIa^1$. In a particular embodiment $R_1$ is the group of formula $IIa2$. In a particular embodiment $R_1$ is the group of formula $IIa^3$. In a particular embodiment $R_1$ is the group of formula $IIa^4$.

When $R_1$ is the group of formula IIb, $R_7$ may be H or methyl. In a particular embodiment $R_1$ is benzothiophene. In another particular embodiment, $R_1$ is indole. In another particular embodiment $R_1$ is N-methyl indole. In another particular embodiment $R_1$ is benzofuran. In another particular embodiment $R_1$ is 2,3-dihydro-benzofuran.

When $R_1$ is the group of formula IIc, m is 0 or 1; $R_7$ is H, alkyl or halogen; $R_8$ is H, alkyl or aryl; and $R_9$ is H or methyl. In a particular embodiment $R_1$ is the group of formula $IIc^1$:

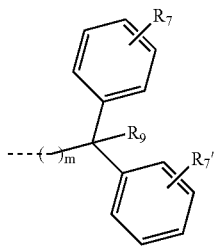

wherein $R_7$ and $R_{7'}$ are each independently H, alkyl, alkoxy, halogen, hydroxyl, mercapto, carboxyl, amino, nitro, aryl, aryloxy, aralkyl, cycloalkyl, cycloalkylalkyl, heteroaryl, or heteroaralkyl; $R_9$ is H or alkyl; and m is 0 or 1. In a particular embodiment, $R_9$ is H. In another particular embodiment $R_9$ is methyl. In another particular embodiment m is 0. In another particular embodiment m is 1. In a particular embodiment m is 0, $R_7$ and $R_{7'}$ are both H and $R_9$ is H. In another particular embodiment, m is 1, $R_7$ and $R_{7'}$ are both H and $R_9$ is H. in another particular embodiment, m is 0, $R_7$ and $R_{7'}$ are both H and $R_9$ is methyl. In another particular embodiment, m is 1, $R_7$ and $R_{7'}$ are both H and $R_9$ is methyl.

When $R_1$ is the group IId, $R_7$ is H, alkyl or aryl; m is 0 or 1; $R_9$ and $R_{9'}$ are independently H or alkyl. In a particular embodiment m is 0; $R_7$ is H or aryl. In a particular embodiment m is 0 and $R_7$ is H. In another particular embodiment m is 0 and $R_7$ is 2-phenyl. In another embodiment m is 1; $R_7$ is H; and $R_9$ and $R_{9'}$ are both H. In another embodiment m is 1; $R_7$ is H and $R_9$ and $R_{9'}$ are both methyl.

When L is a bond, $R_1$ is may be alkyl, cycloalkylalkyl, aryl, aralkyl, a heterocycle or heterocyclylalkyl each optionally substituted with halogen hydroxyl, mercapto, carboxyl, alkyl, haloalkyl, amino, nitro, aryl and heteroaryl. In this particular embodiment, $R_1$ is heteroaryl optionally substituted with aryl or heteroaryl. In a particular embodiment $R_1$ is

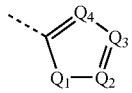

wherein $Q_1$ is $NR_{11}$, O or S; $Q_2$, $Q_3$ and $Q_4$ are independently $CR_{11}$ or N; wherein $R_{11}$ is H, alkyl, aryl, cycloalkyl or a heterocycle optionally substituted with halogen hydroxyl, mercapto, carboxyl, alkyl, haloalkyl, amino, nitro, aryl or heteroaryl. In such an embodiment, $R_{11}$ may be an optionally substituted phenyl or pyridyl group. In a particular embodiment $R_1$ is

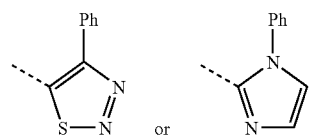

In a particular embodiment when L is —$C(X_3)NR_{12}$, $R_{12}$ is H, alkyl, cycloalkylalkyl, aryl, aralkyl, a heterocycle or heterocyclylalkyl each optionally substituted with halogen hydroxyl, mercapto, carboxyl, alkyl, haloalkyl, amino, nitro, aryl and heteroaryl. In this particular embodiment, $R_{12}$ is aryl optionally substituted with halogen, hydroxyl or haloalkyl. In a particular embodiment $R_{12}$ is phenyl.

$R_2$ is alkyl, cycloalkyl, cycloalkylalkyl, aryl, aralkyl, a heterocycle or heterocyclylalkyl. In a particular embodiment $R_2$ is alkyl or cycloalkyl. In an embodiment of the invention $R_2$ is t-butyl, isopropyl, cyclohexyl, cyclopentyl or phenyl. In a particular embodiment, $R_2$ is cyclohexyl. In another embodiment $R_2$ is tetrahydropyran-4-yl. In another particular embodiment, $R_2$ is isopropyl (i.e. the valine amino acid side chain). In another particular embodiment, $R_2$ is t-butyl. In a particular embodiment $R_2$ is oriented such that the amino acid, or amino acid analogue, which it comprises is in the L-configuration.

$R_3$ is H or alkyl. In a particular embodiment $R_3$ is H or methyl, ethyl, propyl or isopropyl. In a particular embodiment $R_3$ is H or methyl. In another particular embodiment $R_3$ is methyl. In another particular embodiment, $R_3$ is t-butyl. In another particular embodiment $R_3$ is oriented such that the amino acid, or amino acid analogue, which it comprises is in the L-configuration.

$R_4$ and $R_{4'}$ are independently H, alkyl, aryl, aralkyl, cycloalkyl, cycloalkylalkyl, heteroaryl, or heteroaralkyl wherein each is optionally substituted with halogen, hydroxyl, mercapto, carboxyl, alkyl, alkoxy, amino and nitro. In a particular embodiment $R_4$ and $R_{4'}$ are both H. In another particular embodiment $R_4$ is methyl and $R_{4'}$ is H. In a particular embodiment, $R_{4'}$ is H and $R_4$ is H, alkyl, aryl, aralkyl, cycloalkyl, cycloalkylalkyl, heteroaryl or heteroaralkyl. In a particular embodiment $R_4$ is a group selected from the group consisting of:

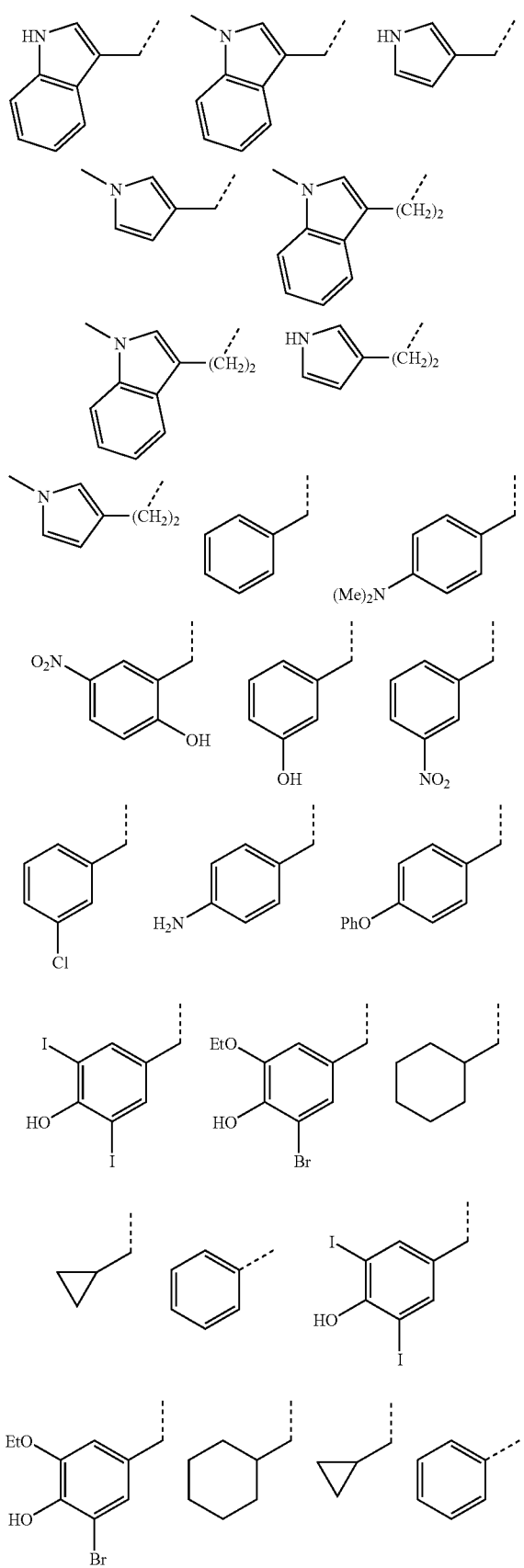

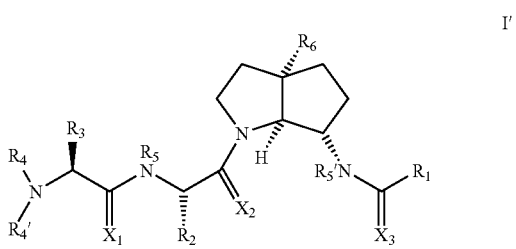

$R_5$ and $R_{5'}$ are each independently H or alkyl. In a particular embodiment, $R_5$ and $R_{5'}$ are H or methyl. In a particular embodiment, $R_5$ is H and $R_{5'}$ is methyl. In another particular embodiment, $R_5$ is methyl and $R_{5'}$ is H. In another particular embodiment $R_5$ and $R_{5'}$ are both methyl. In another particular embodiment, $R_5$ and $R_{5'}$ are both H.

$R_6$ is H or alkyl. In a particular embodiment, $R_6$ is H or methyl. In a particular embodiment $R_6$ is H.

Compounds of the invention contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention. In a particular embodiment, compounds of the invention have the following stereochemical configuration of formula I'

I'

The invention also encompasses prodrugs of the compounds described above. Suitable prodrugs where applicable include known amino-protecting and carboxy-protecting groups which are released, for example hydrolyzed, to yield the parent compound under physiologic conditions. A particular class of prodrugs are compounds in which a nitrogen atom in an amino, amidino, aminoalkyleneamino, iminoalkyleneamino or guanidino group is substituted with a hydroxy (OH) group, an alkylcarbonyl (—CO—R) group, an alkoxycarbonyl (—CO—OR), an acyloxyalkyl-alkoxy-carbonyl (—CO—O—R—O—CO—R) group where R is a monovalent or divalent group and as defined above or a group having the formula —C(O)—O—CP1P2-haloalkyl, where P1 and P2 are the same or different and are H, lower alkyl, lower alkoxy, cyano, halo lower alkyl or aryl. In a particular embodiment, the nitrogen atom is one of the nitrogen atoms of the amidino group of the compounds of the invention. These prodrug compounds are prepared reacting the compounds of the invention described above with an activated acyl compound to bond a nitrogen atom in the compound of the invention to the carbonyl of the activated acyl compound. Suitable activated carbonyl compounds contain a good leaving group bonded to the carbonyl carbon and include acyl halides, acyl amines, acyl pyridinium salts, acyl alkoxides, in particular acyl phenoxides such as p-nitrophenoxy acyl, dinitrophenoxy acyl, fluorophenoxy acyl, and difluorophenoxy acyl. The reactions are generally exothermic and are carried out in inert solvents at reduced temperatures such as −78 to about 50C. The reactions are usually also carried out in the presence of an inorganic base such as potassium carbonate or sodium bicarbonate, or an organic base such as an amine, including pyridine, triethylamine, etc. One manner of preparing prodrugs is described in U.S. Ser. No. 08/843,369 filed Apr. 15, 1997 (corresponding to PCT publication WO9846576) the contents of which are incorporated herein by reference in their entirety.

Particular compounds of formula I include the following:

1
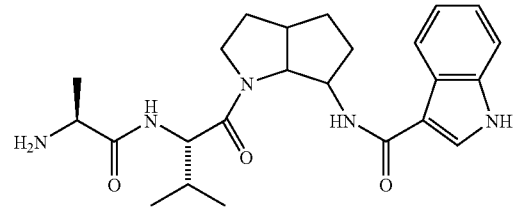

2
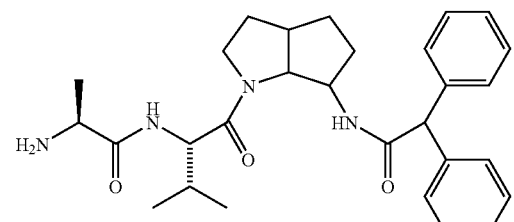

3
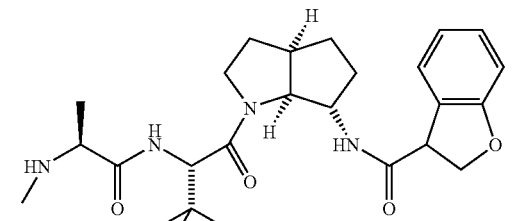

4
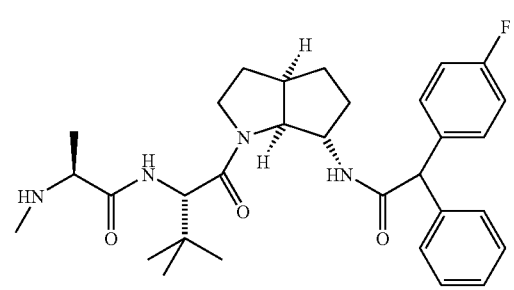

-continued

5
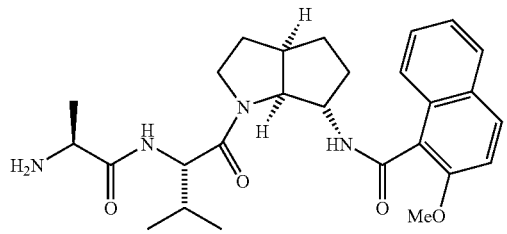

6
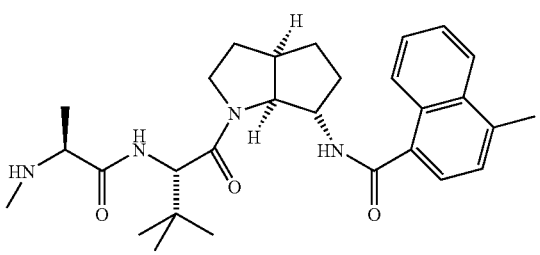

7
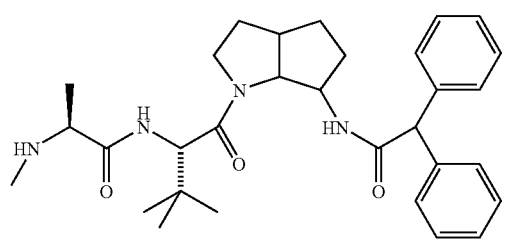

8
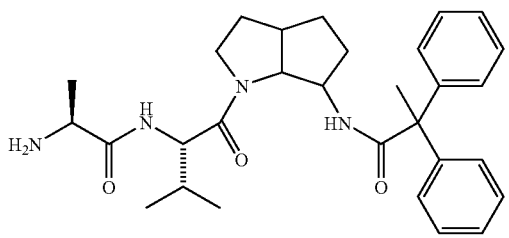

9
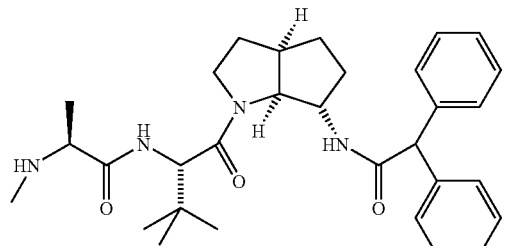

10
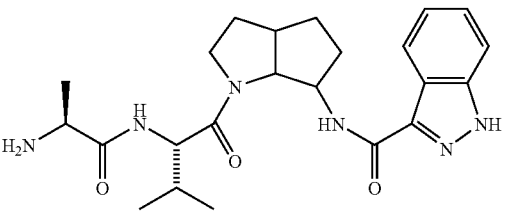

-continued
11
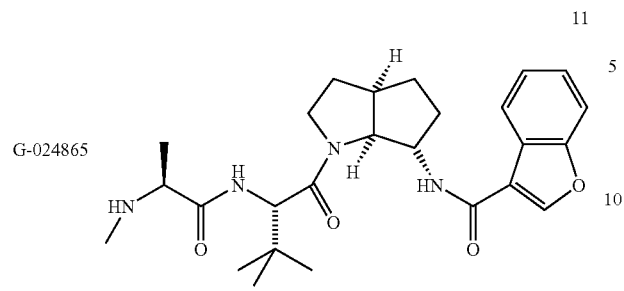
G-024865
12
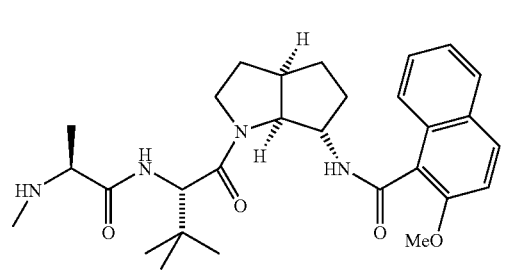
13
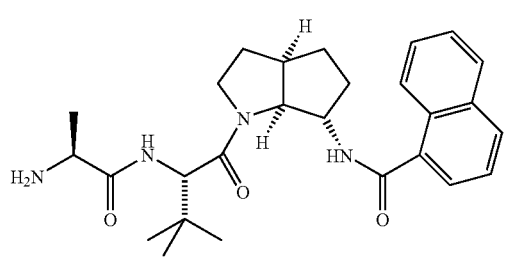
14
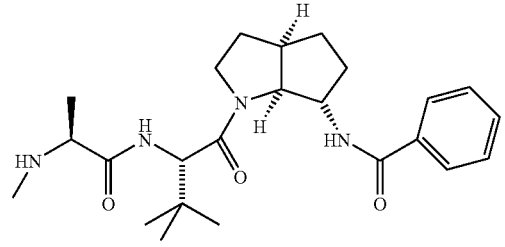
15
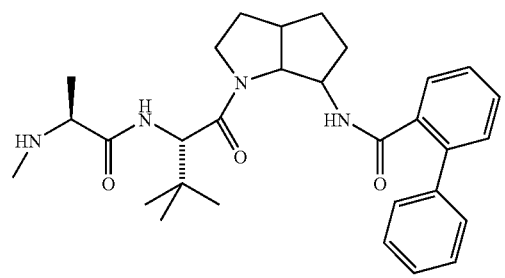
16
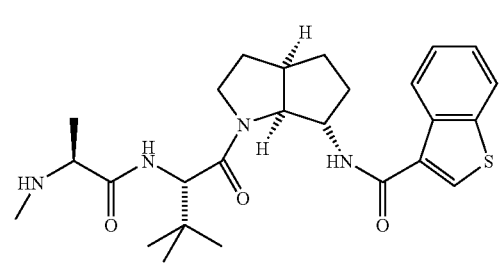
-continued
17
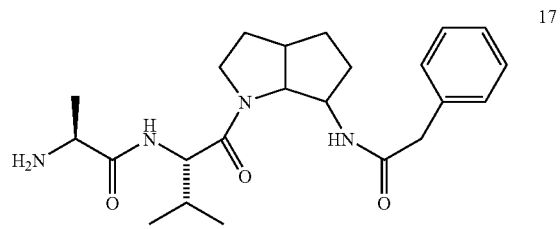
18
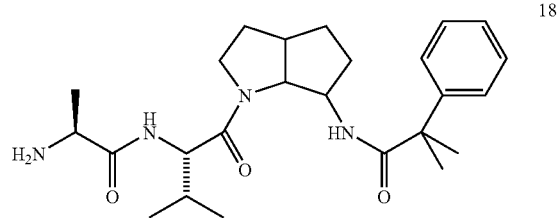
19
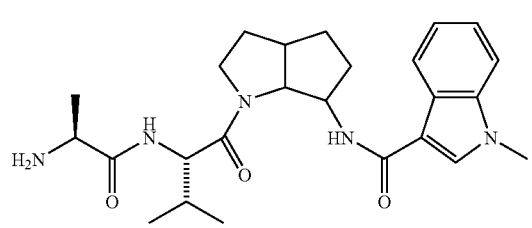
20
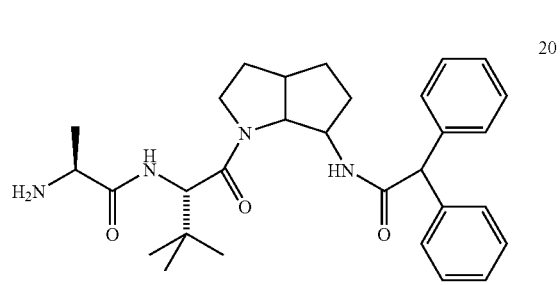
21
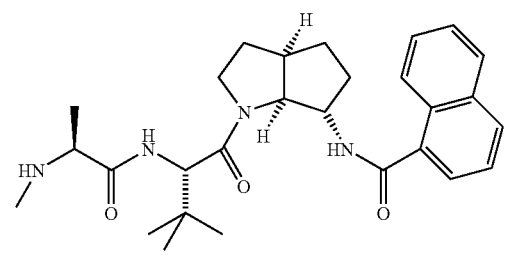
22
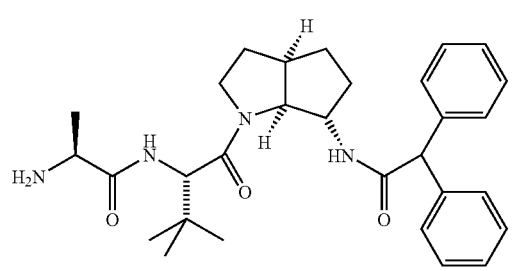

-continued
23
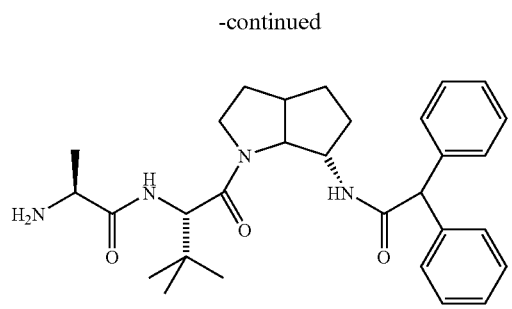
24
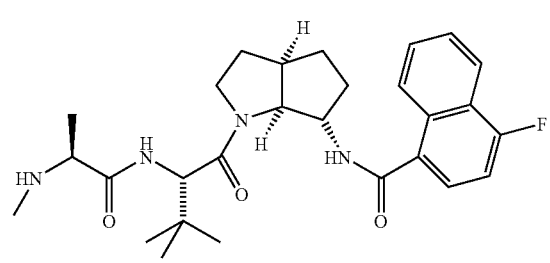
25
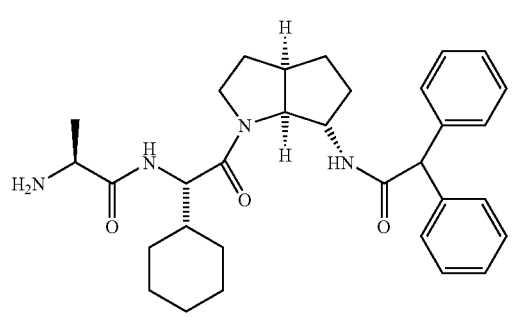
26
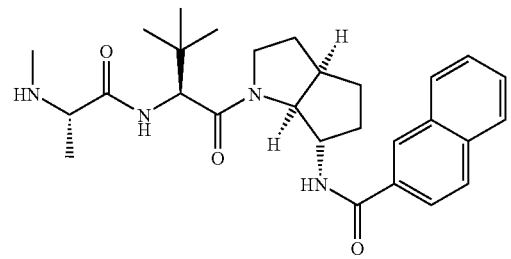
27
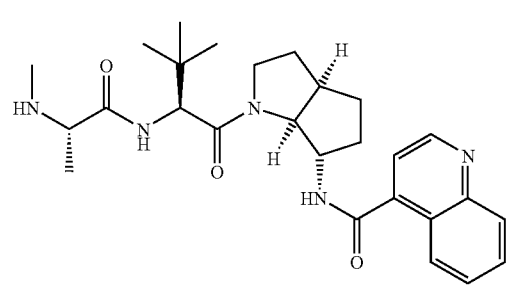
-continued
28
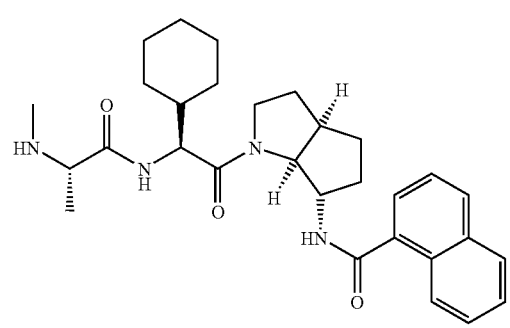
29
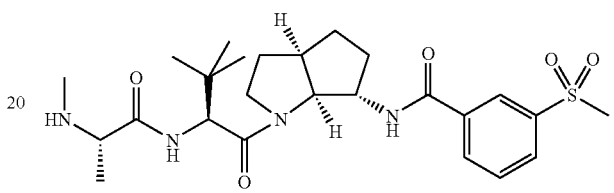
30
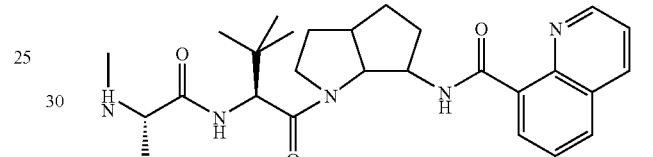
31
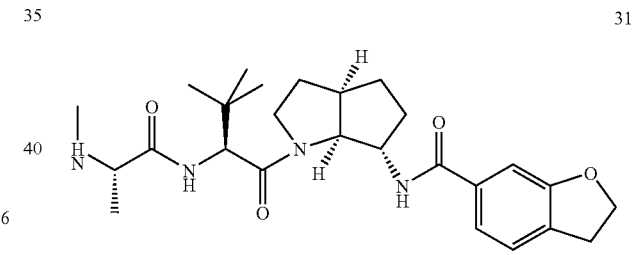
32
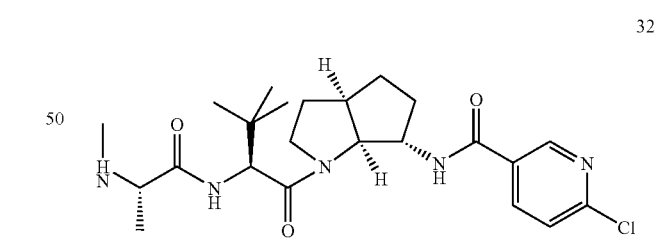
33
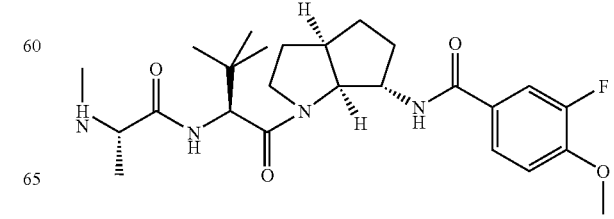

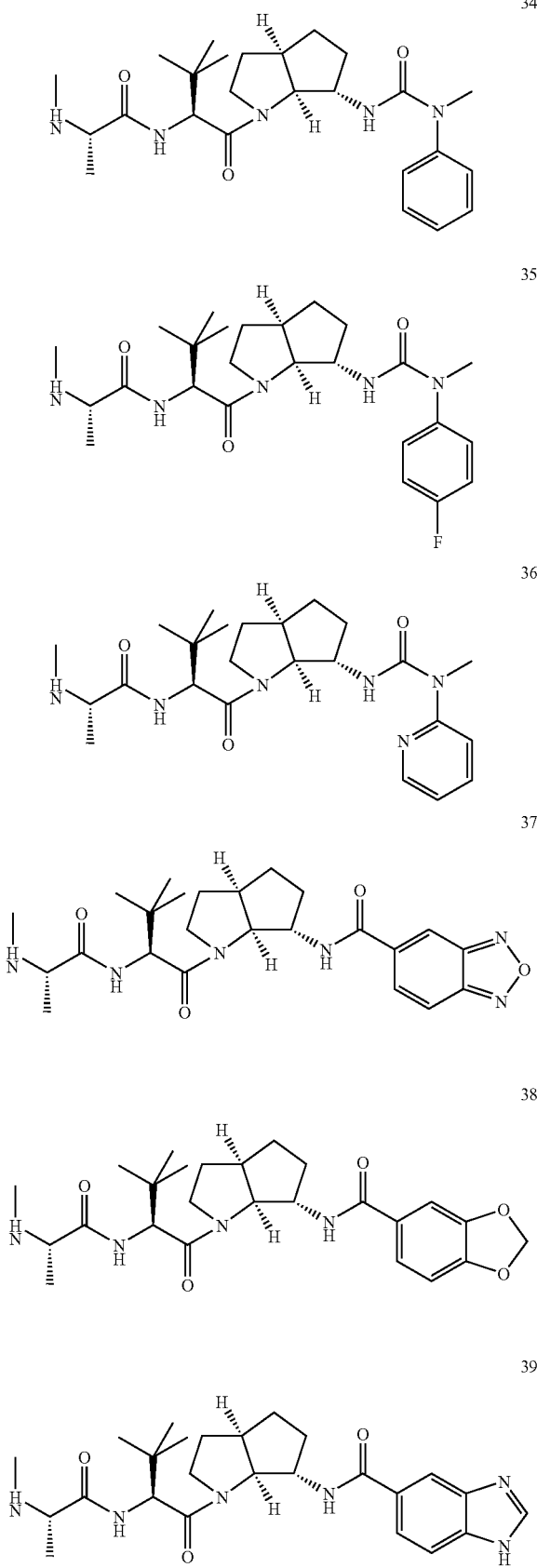

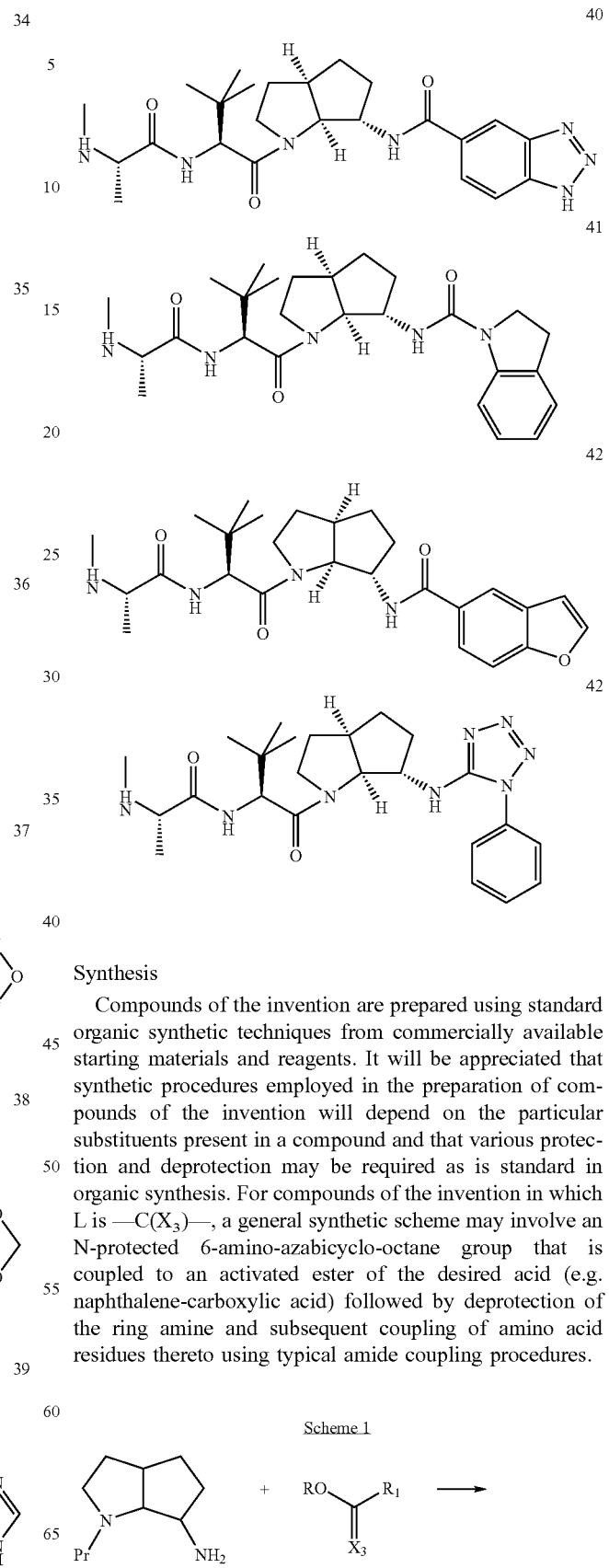

Synthesis

Compounds of the invention are prepared using standard organic synthetic techniques from commercially available starting materials and reagents. It will be appreciated that synthetic procedures employed in the preparation of compounds of the invention will depend on the particular substituents present in a compound and that various protection and deprotection may be required as is standard in organic synthesis. For compounds of the invention in which L is —C(X₃)—, a general synthetic scheme may involve an N-protected 6-amino-azabicyclo-octane group that is coupled to an activated ester of the desired acid (e.g. naphthalene-carboxylic acid) followed by deprotection of the ring amine and subsequent coupling of amino acid residues thereto using typical amide coupling procedures.

Scheme 1

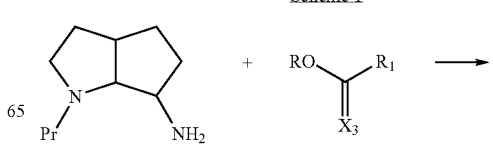

-continued

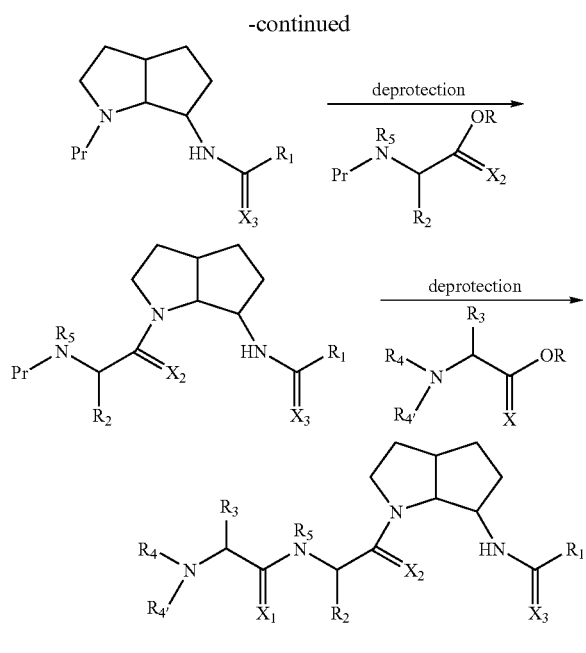

The N-protected 6-amino-azabicyclo-octane intermediate may be prepared according to the procedures described in Cary et al, Tetrahedron Letters, 1989, 30:5547 illustrated in scheme 2 below. In general, an activated ester of cyclopentene acetic acid is coupled to methylbenzyl amine. The methylbenzyl group serves as an amine protecting for the ring product prior to coupling to amino acid residues. The resulting amide is reduced with lithium aluminum hydride to form a secondary amine which is then reacted with N-bromosuccinamide. The resulting N-bromo amine is cyclized with a catalytic amount of cuprous bromide to generated the 6-bromo substituted azabicyclo-octane ring. The ring is then reacted with ammonium hydroxide to convert the 6-bromo group to the corresponding 6-amino ring intermediate which then may used in the synthesis of the compounds of the invention.

Scheme 2

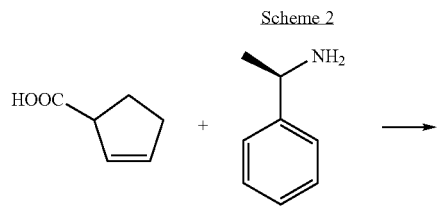

-continued

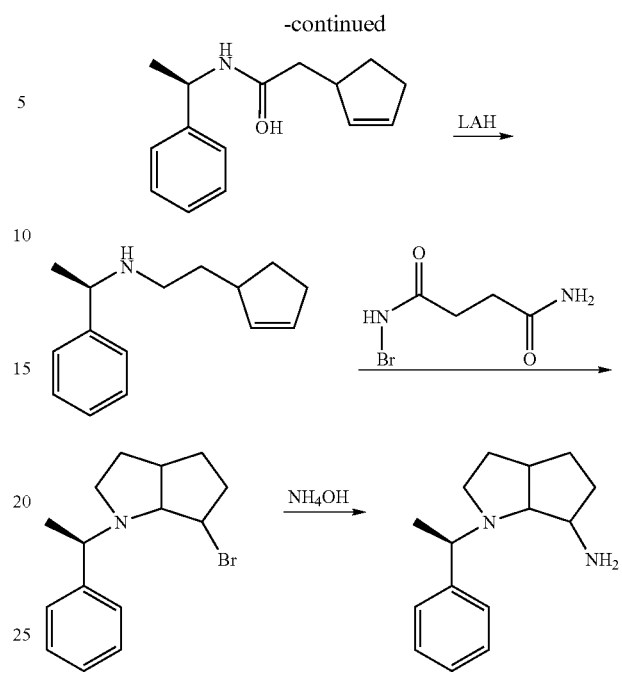

In a particular embodiment, the methyl benzyl amine is enantiomerically pure. Use of such a chiral auxiliary enables the convenient separation of the diastereomers of the azabicyclo-octane ring, for example RP-HPLC or silica gel column. Separation of the diastereomers may be performed with the 6-bromo substituted ring or the 6-amino substituted ring prior to removal of the chiral auxiliary protecting group.

Alternatively, the compounds of the invention may be prepared according to the general Scheme 3, by sequential coupling of amino acids residues incorporating $R_2$ and $R_3$ to the azabicyclo-octane ring followed by coupling an $R_4$-containing acid to the 6-amino group on the azabicyclo-octane ring. In this method, the starting azabicyclo-octane ring is protected at the primary 6-amino substituent, for example with a Teoc group (trimethylsilylethyloxycarbonyl) followed by deprotection of the secondary ring amine. Using standard peptide coupling methods, the resulting deprotected ring amine is coupled with an $R_2$-containing residue and then an $R_3$-containing residue. The Teoc group is then removed with TASF (tris(dimethylamino)sulfonium difluorotrimethylsilicate) and the deprotected 6-amino group is coupled with an $R_4$-containing acid.

Scheme 3

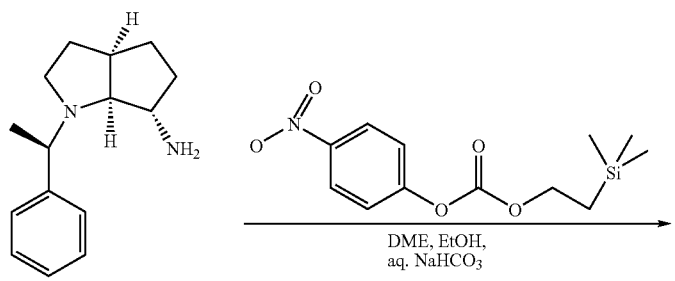

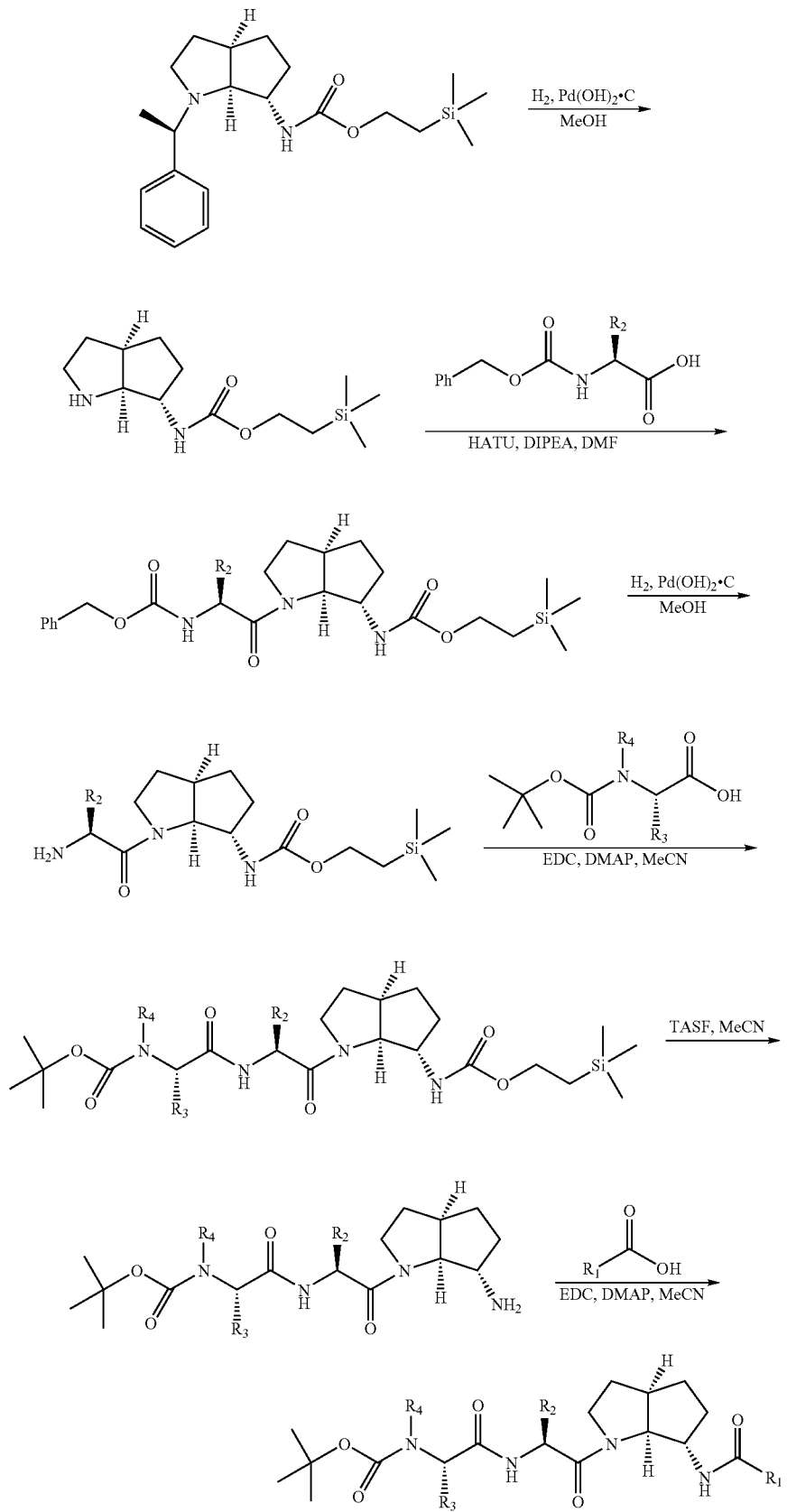

For compounds of the invention in which L is —C(X₃)O—, i.e. a carbamate, a general synthetic scheme may involve reacting the N-protected 6-amino-azabicyclo-octane intermediate with a chloroformate of R₁ (Cl—C(O)O—R₁).

For compounds of the invention in which L is —C(X₃)NR₁₂—, i.e. a urea, a general synthetic scheme may involve reacting the N-protected 6-amino-azabicyclo-octane intermediate with para-nitrophenylchloroformate followed by reacting the resulting carbamate with primary or secondary amine NR₁R₁₂ under strong basic conditions as illustrated in scheme 4.

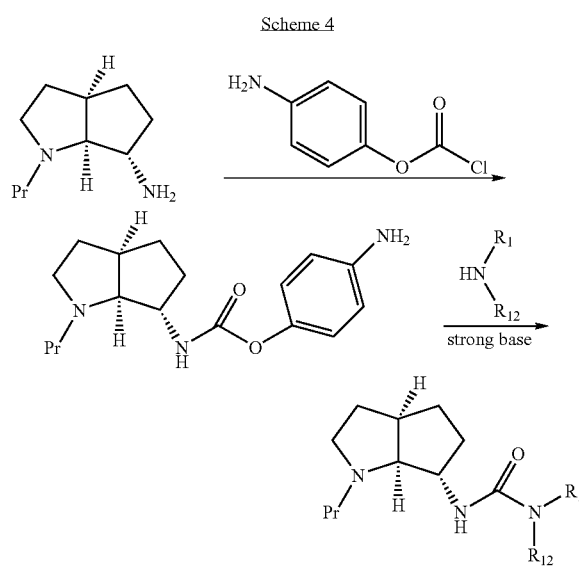

Compounds in which L is a bond, i.e. R₁ and the nitrogen from which it depends form an amine, maybe prepared by reductive amination. Alternatively such compounds may be prepared by reacting the N-protected 6-amino-azabicyclo-octane group with a methylsulfonate ester of the R₁ group, for instance when R₁ is an aliphatic group such as alkyl, alkenyl or alkynyl. When R₁ is aryl or heteroaryl such compounds may be prepared by reacting the N-protected 6-amino-azabicyclo-octane group with a methylsulfonyl-substituted R₁ compound according to the procedures described in Blass et, al. Bioorg. Med. Chem. Lett., 2000, 10:1543 and Bakhtiar, et al J. Chem. Soc. Perkin Trans. 1. 1994, 3:239. For example, when L is a bond and R₁ is 1-phenyl-1H-imidazol-2-yl the compound may be prepared according to the following scheme 5.

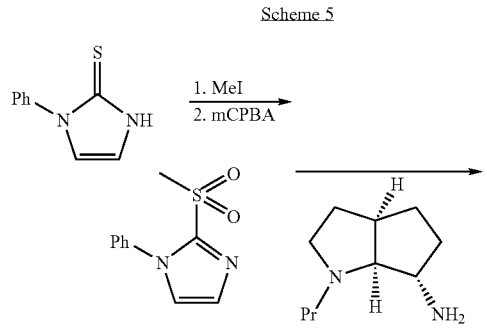

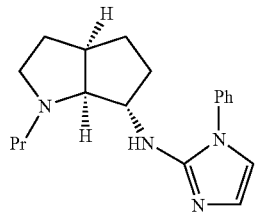

in which 1-phenyl-1,3-dihydro-imidazole-2-thione is reacted with methyl iodide followed by oxidation with m-chloroperoxybenzoic acid to give the methyl sulfonyl which is reacted with the N-protected 6-amino-azabicyclo-octane group.

In another example, when L is a bond and R₁ is 4-phenyl-[1,2,3]thiadiazol-5-yl, the compound may be prepared according to the following scheme 6 which are described in Masuda et. al., J. Chem. Soc. Perkin. Trans. 1, 1981, (5) 1591.

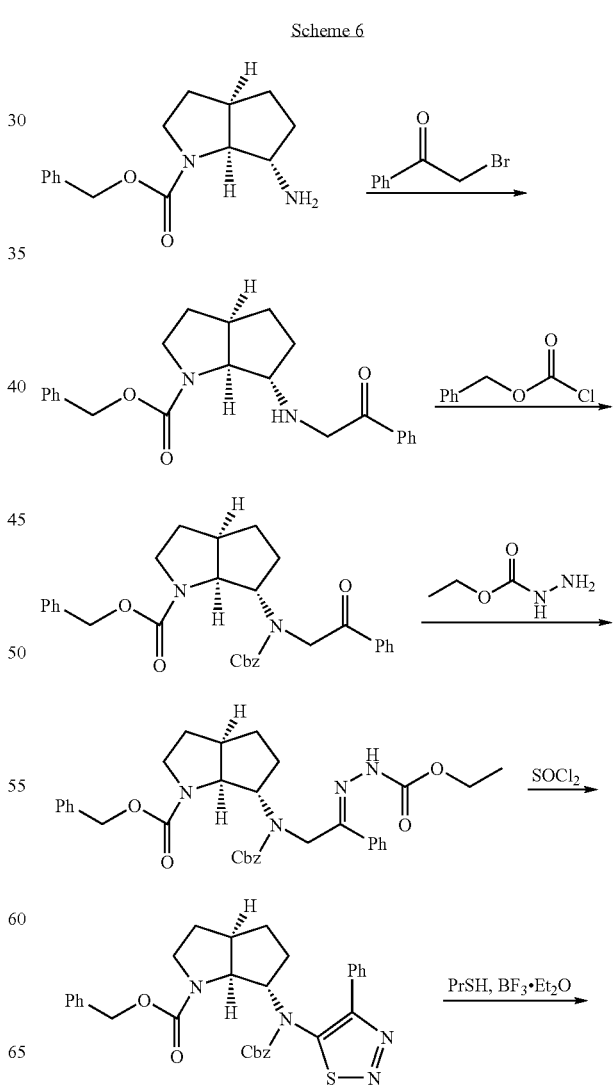

-continued

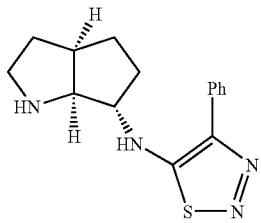

Utility

The compounds of the invention inhibit the binding of IAP protein e.g. XIAP and ML-IAP, in cells to caspases, e.g. caspases 3, 7 and/or 9. Accordingly, the compounds of the invention are useful for inducing apoptosis in cells or sensitizing cells to apoptotic signals, in particular cancer cells that overexpress IAP proteins. More broadly, the compounds can be used for the treatment of all cancer types which fail to undergo apoptosis. Examples of such cancer types include neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma.

Compounds of the invention are useful for sensitizing cells to apoptotic signals. Accordingly, the compounds may be administered prior to, concomitantly with, or following administration of radiation therapy or cytostatic or antineoplastic chemotherapy. Suitable cytostatic chemotherapy compounds include, but are not limited to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphtheria toxin; (Vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, STI571 (CPG 57148B) or UCN-01 (7-hydroxystaurosporine); (x) miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists. In a particular embodiment, compounds of the present invention are coadministered with a cytostatic compound selected from the group consisting of cisplatin, doxorubicin, taxol, taxotere and mitomycin C. A particular cytostatic compound is doxorubicin.

Another class of active compounds which can be used in the present invention are those which are able to sensitize for or induce apoptosis by binding to death receptors ("death receptor agonists"). Such agonists of death receptors include death receptor ligands such as tumor necrosis factor α (TNF-α), tumor necrosis factor β (TNF-β, lymphotoxin-α), LT-β (lymphotoxin-β), TRAIL (Apo2L, DR4 ligand), CD95 (Fas, APO-1) ligand, TRAMP (DR3, Apo-3) ligand, DR6 ligand as well as fragments and derivatives of any of said ligands. In a particular embodiment, the death receptor ligand is TNF-α. In a particular embodiment the death receptor ligand is Apo2L/TRAIL. Furthermore, death receptors agonists comprise agonistic antibodies to death receptors such as anti-CD95 antibody, anti-TRAIL-R1 (DR4) antibody, anti-TRAIL-R2 (DR5) antibody, anti-TRAIL-R3 antibody, anti-TRAIL-R4 antibody, anti-DR6 antibody, anti-TNF-R1 antibody and anti-TRAMP (DR3) antibody as well as fragments and derivatives of any of said antibodies.

For the purpose of sensitizing cells for apoptosis, the compounds of the present invention can be also used in combination with radiation therapy. The phrase "radiation therapy" refers to the use of electromagnetic or particulate radiation in the treatment of neoplasia. Radiation therapy is based on the principle that high-dose radiation delivered to a target area will result in the death of reproducing cells in both tumor and normal tissues. The radiation dosage regimen is generally defined in terms of radiation absorbed dose (rad), time and fractionation, and must be carefully defined by the oncologist. The amount of radiation a patient receives will depend on various consideration but the two most important considerations are the location of the tumor in relation to other critical structures or organs of the body, and the extent to which the tumor has spread. Examples of radiotherapeutic agents are provided in, but not limited to, radiation therapy and is known in the art (Hellman, Principles of Radiation Therapy, Cancer, in Principles I and Practice of Oncology, 24875 (Devita et al., 4th ed., vol 1, 1993). Recent advances in radiation therapy include three-dimensional conformal external beam radiation, intensity modulated radiation therapy (IMRT), stereotactic radiosurgery and brachytherapy (interstitial radiation therapy), the latter placing the source of radiation directly into the tumor as implanted "seeds". These newer treatment modalities deliver greater doses of radiation to the tumor, which accounts for their increased effectiveness when compared to standard external beam radiation therapy.

Ionizing radiation with beta-emitting radionuclides is considered the most useful for radiotherapeutic applications because of the moderate linear energy transfer (LET) of the ionizing particle (electron) and its intermediate range (typically several millimeters in tissue). Gamma rays deliver dosage at lower levels over much greater distances. Alpha particles represent the other extreme, they deliver very high LET dosage, but have an extremely limited range and must, therefore, be in intimate contact with the cells of the tissue to be treated. In addition, alpha emitters are generally heavy metals, which limits the possible chemistry and presents undue hazards from leakage of radionuclide from the area to be treated. Depending on the tumor to be treated all kinds of emitters are conceivable within the scope of the present invention.

Furthermore, the present invention encompasses types of non-ionizing radiation like e.g. ultraviolet (UV) radiation, high energy visible light, microwave radiation (hyperthermia therapy), infrared (IR) radiation and lasers. In a particular embodiment of the present invention UV radiation is applied.

The invention also includes pharmaceutical compositions or medicaments containing the compounds of the invention and a therapeutically inert carrier, diluent or excipient, as well as methods of using the compounds of the invention to prepare such compositions and medicaments. Typically, the compounds of formula I used in the methods of the invention are formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but may range anywhere from about 3 to about 8. Formulation in an acetate buffer at pH 5 is a suitable embodiment. The inhibitory compound for use herein may be sterile. The compound ordinarily will be stored as a solid composition, although lyophilized formulations or aqueous solutions are acceptable.

The composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit IAP interaction with caspases, induce apoptosis or sensitize a malignant cell to an apoptotic signal. Such amount is preferably below the amount that is toxic to normal cells, or the mammal as a whole.

Generally, the initial pharmaceutically effective amount of the compound of the invention administered parenterally per dose will be in the range of about 0.01-100 mg/kg, for example, about 0.1 to 20 mg/kg of patient body weight per day, with the typical initial range of compound used being 0.3 to 15 mg/kg/day. Oral unit dosage forms, such as tablets and capsules, may contain from about 25 to about 1000 mg of the compound of the invention.

The compound of the invention may be administered by any suitable means, including oral, topical, transdermal, parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution is typically filtered, e.g. using a 0.2 micron filter, to remove impurities and contaminants.

EXAMPLES

The invention will be more fully understood by reference to the following examples. They should not, however, be construed as limiting the scope of the invention. Abbreviations used herein are as follows:

DIPEA: diisopropylethylamine;
DMAP: 4-dimethylaminopyridine;
DME: 1,2-dimethoxyethane;
DMF: dimethylformamide;
EDC: 1-ethyl-3-(3-dimethylaminopropyl)carbodiimide;
HATU: O-(7-Azobenzotriazol-1-yl)-1,1,3,3-tetramethyluronium hexafluorophosphate;
NBS: N-bromosuccinamide;
TASF: tris(dimethylamino)sulfonium difluorotrimethylsilicate;
THF: tetrahydrofuran;

Example 1

The 2-azabicyclo[3.3.0]octane rings were prepared according to the procedures in Corey et al, Tetrahedron Letters, 1989, 30:5547.

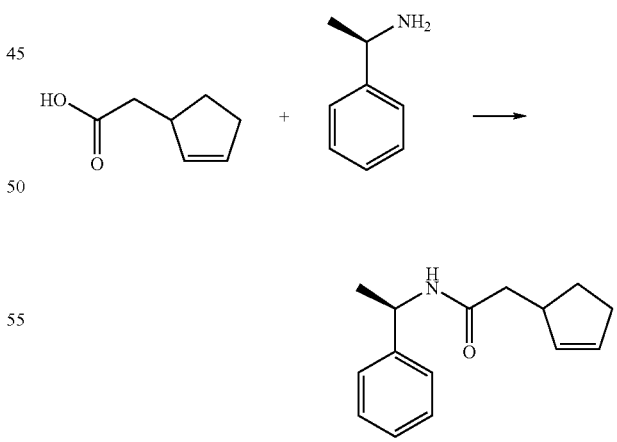

EDC (38.34 g, 200 mmol), DMAP (2.44 g, 20 mmol), cyclopentene acetic acid (25.0 g, 198 mmol), and R-α-methyl benzyl amine (25 mL, 196 mmol) were added sequentially to $CH_2Cl_2$ (500 mL). The solution was maintained at rt. for 2 h, then washed with 1N HCl (3×100 mL), 1N NaOH (3×100 mL), brine (1×100 mL), dried (Na$_2$SO$_4$), filtered, and concentrated to afford 43.7 g (97%) of amide 3 as a colorless solid.

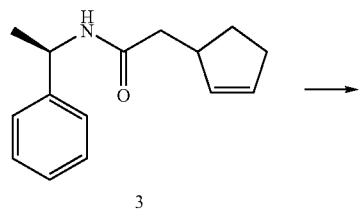

3

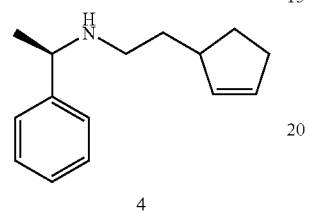

4

To a solution of amide 3 (43.6 g, 190 mmol) in THF (430 mL) at 0° C. was added lithium aluminum hydride (200 mL of 1.0M solution in THF, 200 mmol) over 2 h. The mixture was allowed to warm to rt, then heated at reflux for 36 h. The mixture was cooled to 0° C., then water (7.6 mL) was added drop wise, followed by 15% NaOH (8 mL) water (24 mL). The resulting mixture was stirred vigorously over night, then filtered through a pad of Celite with THF and 1N NaOH (20 mL). The THF was removed under reduced pressure, and the residue diluted with CH$_2$Cl$_2$, the layers were separated, and the organic layer concentrated to afford a quantitative yield of amine 4 as a colorless oil.

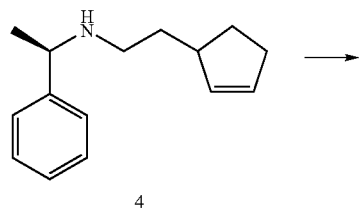

4

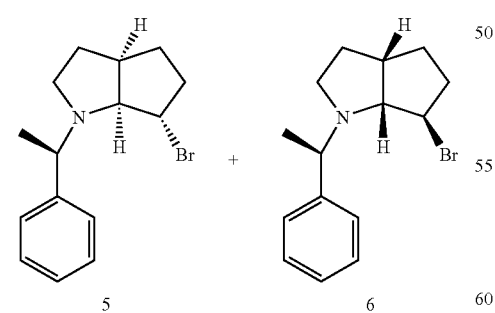

5     6

Amine 4 (950 mg, 4.4 mmol) was treated with N-Bromosuccinamide (980 mg, 5.5 mmol) in hexanes (11 mL) at 0° C. for 2 h with vigorous stirring. Additional NBS (160 mg) was added and stirring continued for 1.5 h at 0° C. The mixture was filtered through a course frit and concentrated.

The residue was dissolved in CH$_2$Cl$_2$ and treated with catalytic CuBr (~1 mg) at 0° C. for 2.5 h. The solvent was removed under reduced pressure to provide a 1:1 mixture of bromides 5 and 6, which was carried on directly.

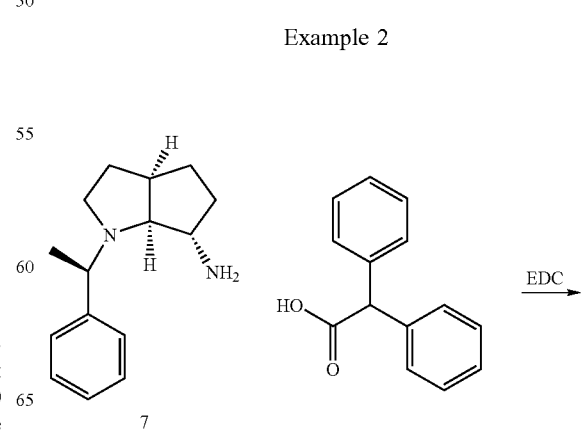

7

The mixture of crude bromides 5 and 6 were dissolved in DME (14 mL) and concentrated NH$_4$OH (7 mL) and heated at 60° C. in a sealed vessel for 18 h. The solvents were removed under reduced pressure, and the residue dissolved in CH$_2$Cl$_2$ (50 mL) and extracted with 1N H$_2$SO$_4$ (1×25 mL). The aq. layer was washed with CH$_2$Cl$_2$ (3×50 mL). The aq. layer was made basic (pH>11) with NaOH(s) and extracted with CH$_2$Cl$_2$ (3×50 mL). The combined organic phases were concentrated and the residue purified by reverse-phase HPLC (C$_{18}$, MeCN—H$_2$O, 0.1% TFA). Fractions containing the product were concentrated under reduced pressure until all of the MeCN was removed, made basic with 1N NaOH (pH>11), and exhaustively extracted with CH$_2$Cl$_2$. The combined organic phases were dried (Na$_2$SO$_4$), filtered and concentrated to provide amine 7 149 mg (29%) as a colorless oil.

Example 2

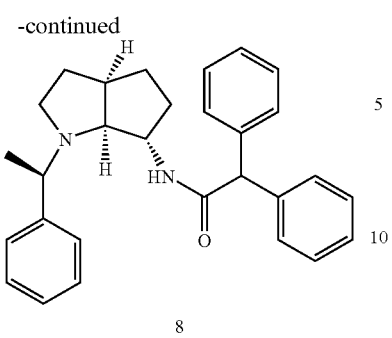

8

Amine 7 (140 mg, 0.61 mmol) was coupled with diphenyl acetic acid (148 mg, 0.7 mmol) following the typical EDC coupling procedure to provide 263 mg (88%) of amide 8 as a colorless oil.

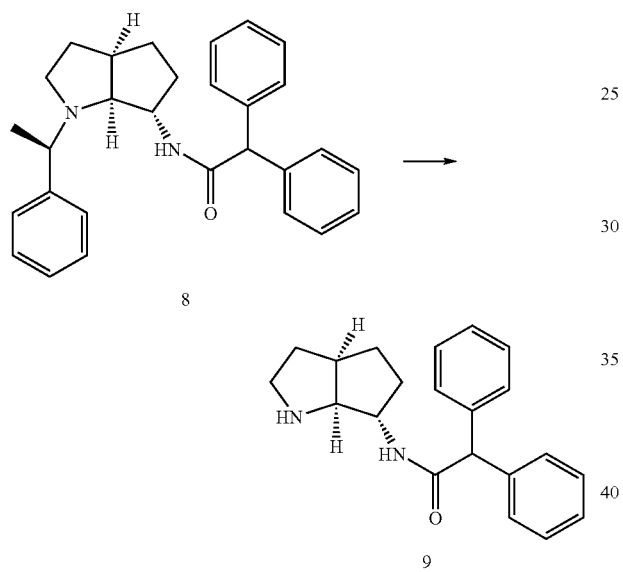

A mixture of benzyl amine 8 (263 mg, 0.62 mmol), acetic acid (71 μL, 1.24 mmol), 20% Pd(OH)$_2$.C (62 mg), and MeOH (6 mL) was maintained under 1 atm. of H$_2$ for 8 h. The mixture was filtered through a pad of Celite, and concentrated. The residue was dissolved in CH$_2$Cl$_2$ (50 mL) and washed with 1N NaOH (3×10 mL), brine (1×10 mL), dried (Na$_2$SO$_4$), filtered, and concentrated to afford 200 mg (100%) of amine 9 as a colorless oil.

Example 3

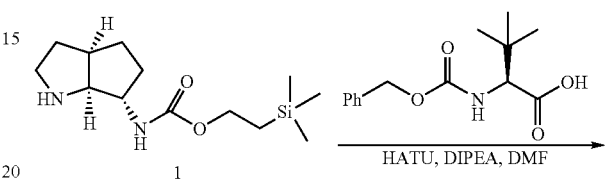

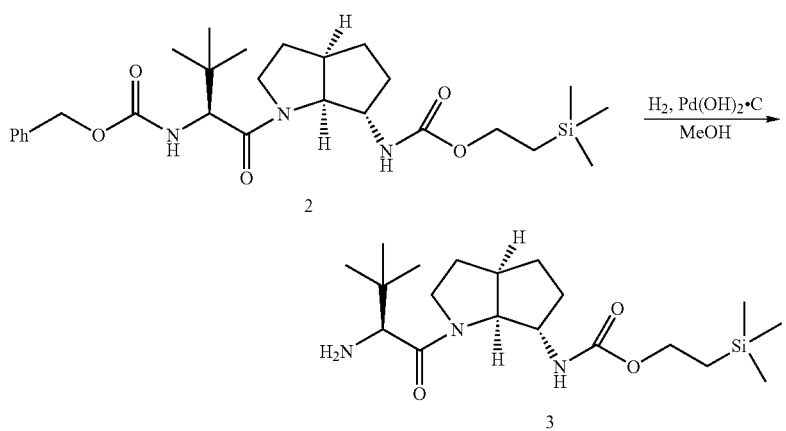

A mixture of secondary amine 1 (166 mg, 0.61 mmol), CbzNt-butylglycine (166 mg, 0.61 mol), HATU (475 mg) DIPEA (1 mL) and DMF (3 ml) was maintained at RT 1 hr. The mixture was diluted with CH$_2$Cl$_2$ (50 mL) and washed with 1N HCl (3×20 mL), dried (Na$_2$SO$_4$), filtered, and concentrated. The residue was purified by flash chromatography (SiO$_2$, 35% ethyl acetate-hexanes) to afford 400 mg (>100%, excess wt. is solvent) of 2 as a colorless oil, which was carried on directly.

A mixture of the amide 2 from above, MeOH (15 ml), AcOH (0.3 ml) and 20% Pd(OH)$_2$.C (150 mg) was stirred vigorously under an atmosphere of H$_2$ for 3 h. The mixture was filtered through Celite, with excess MeOH. The MeOH was removed under reduced pressure, and the residue was dissolved in CH$_2$Cl$_2$ (50 mL) and washed with 0.5N NaOH (3×10 mL), dried (Na$_2$SO$_4$), filtered, and concentrated to afford 169 mg (72% over 2 steps) of amine 3 as a colorless oil.

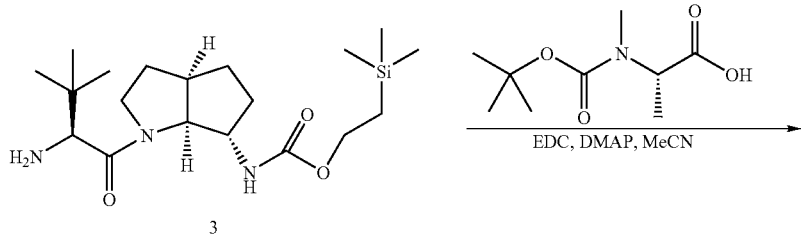

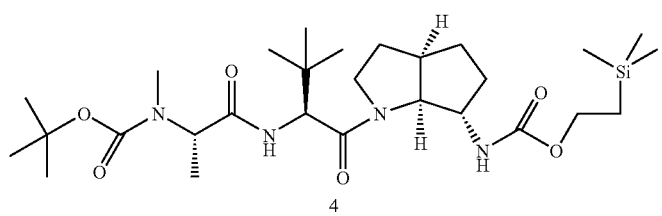

Amine 3 (169 mg, 0.44 mmol) was coupled with N-Boc-N-methyl alanine (108 mg, 0.53 mmol) following the typical EDC coupling procedure to provide 260 mg of protected amine 4 as a colorless oil, which was used with out further purification.

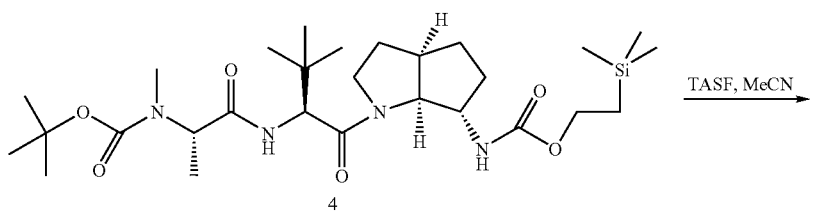

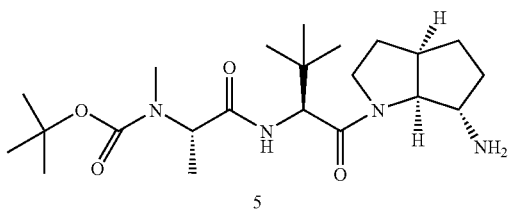

Protected amine 4 (265 mg) was treated with excess TAS-F in MeCN at 50° C. for 4 h. The reaction was diluted with CH$_2$Cl$_2$ (50 mL) and washed with 0.5N NaOH (3×30 mL), dried (Na$_2$SO$_4$), filtered, and concentrated to afford 168 mg (90% over two steps) of amine 5 as a colorless oil.

Example 4
Compound 25
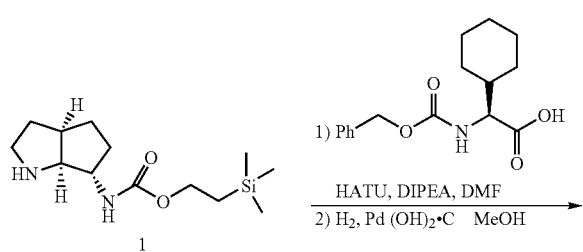
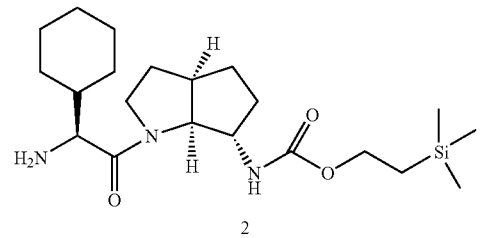
The secondary amine 1 (65 mg) was coupled to Cbz-cyclohexylglycine under the above, then the Cbz group removed under hydrogenolysis to afford 73 mg (74% over 2 steps) of amine 2 as a colorless oil.
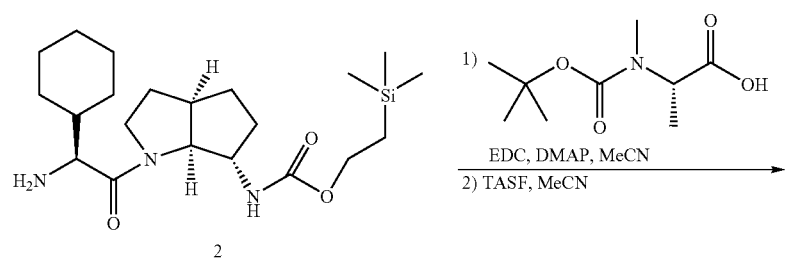
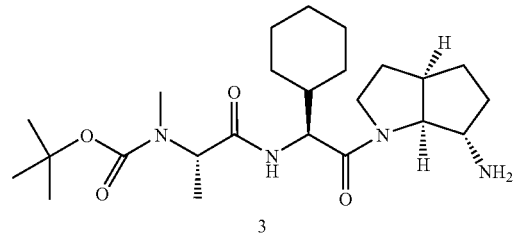
Amine 2 (73 mg) was reacted as above to yield 76 mg (94% over 2 steps) of amine 3.
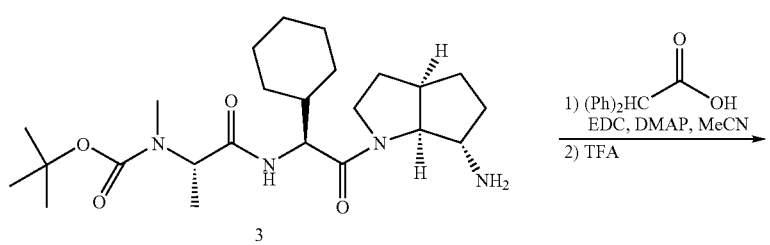

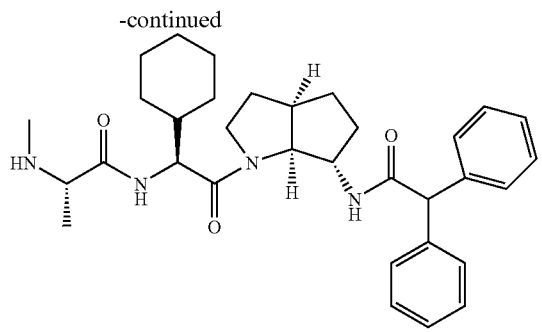

4

Amine 3 (39 mg) was coupled with diphenyl acetic acid under typical EDC coupling conditions, then the Boc group removed under standard conditions. The residue was purified by HPLC to afford 58 mg (34%) of final compound 4 as a colorless solid.

Example 5

Compound 1

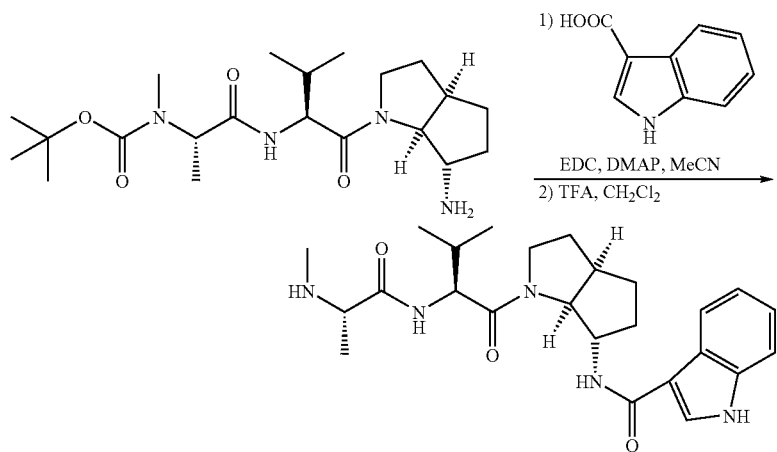

The Boc-protected amine intermediate prepared according to the procedures of example 3 was coupled with the commercially available acid 1H-indole-3-carboxylate under typical EDC coupling conditions followed by Boc group removal and HPLC purification to yield the final compound (31%).

Example 6

Compound 19

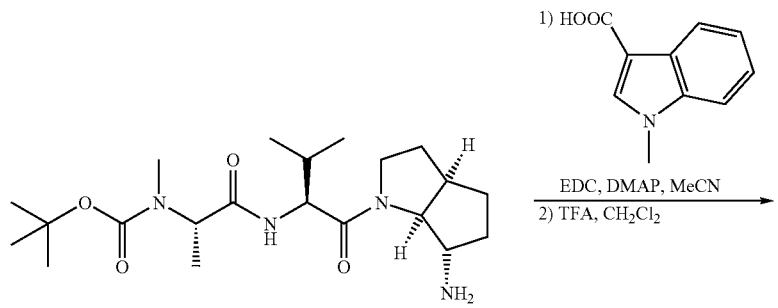

-continued

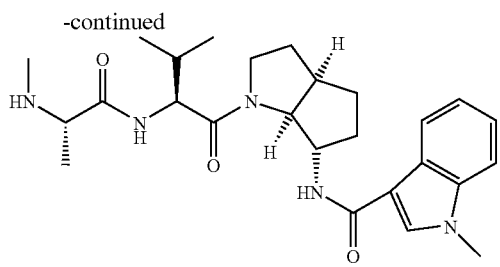

The Boc-protected amine intermediate prepared according to the procedures of example 3 was coupled with the commercially available acid 1-methyl-1H-indole-3-carboxylate under typical EDC coupling conditions followed by Boc group removal and HPLC purification to yield the final compound (39%).

Example 7

Compound 10

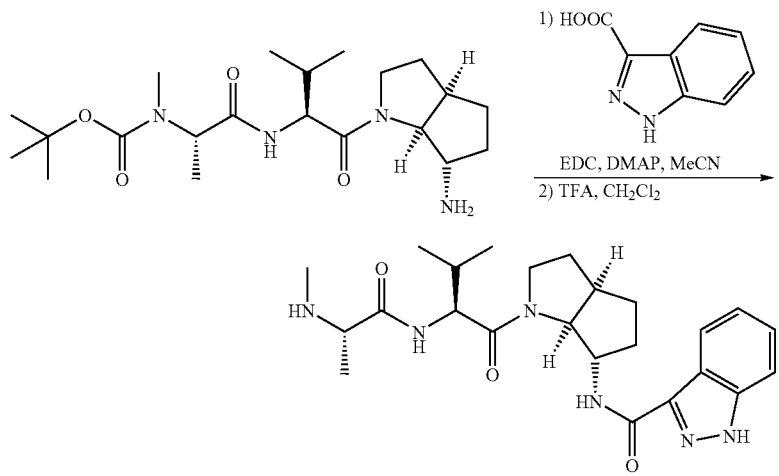

The Boc-protected amine intermediate prepared according to the procedures of example 3 was coupled with the commercially available acid 1-methyl-1H-indazole-3-carboxylate under typical EDC coupling conditions followed by Boc group removal and HPLC purification to yield the final compound (42%).

Example 8

Compound 17

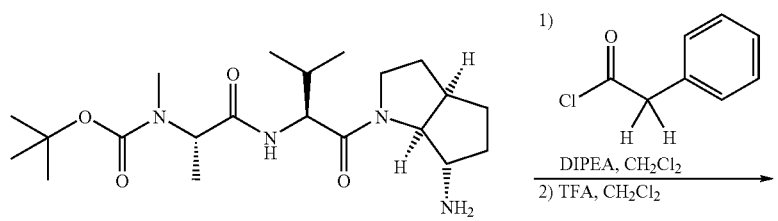

-continued

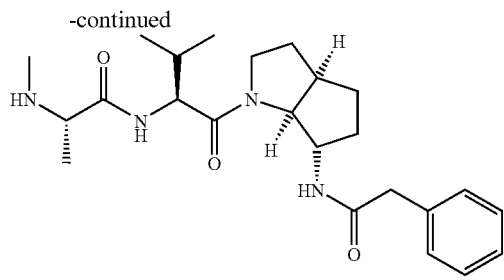

The Boc-protected amine intermediate prepared according to the procedures of example 3 was coupled with the commercially available acid chloride, phenyl-acetyl chloride, followed by Boc removal with TFA and HPLC purification to yield the final compound (39%).

Example 9

Compound 18

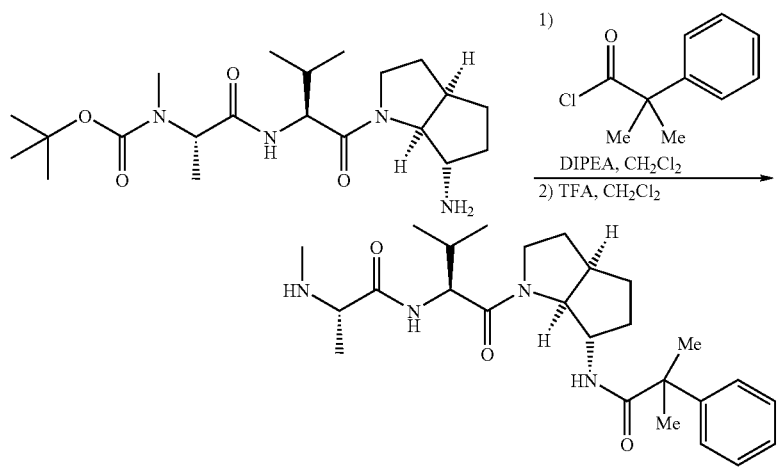

The Boc-protected amine intermediate prepared according to the procedures of example 3 was coupled with the commercially available acid chloride, 2-Methyl-2-phenyl-propionyl chloride, followed by Boc removal with TFA and HPLC purification to yield the final compound (54%).

Example 10

Compound 8

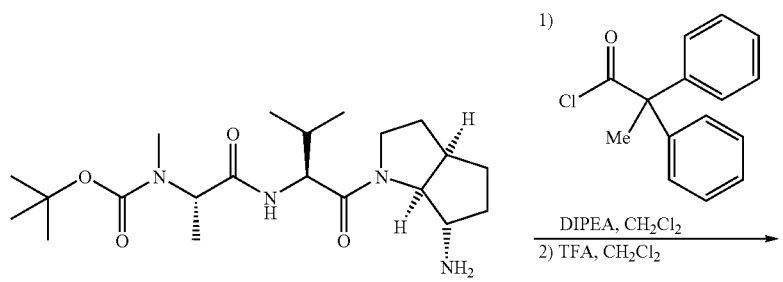

-continued

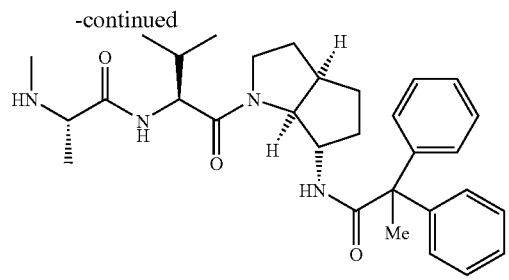

The Boc-protected amine intermediate prepared according to the procedures of example 3 was coupled with the commercially available acid chloride, 2,2-Diphenyl-propionyl chloride, followed by Boc removal with TFA and HPLC purification to yield the final compound (65%).

Example 11

Compound 14

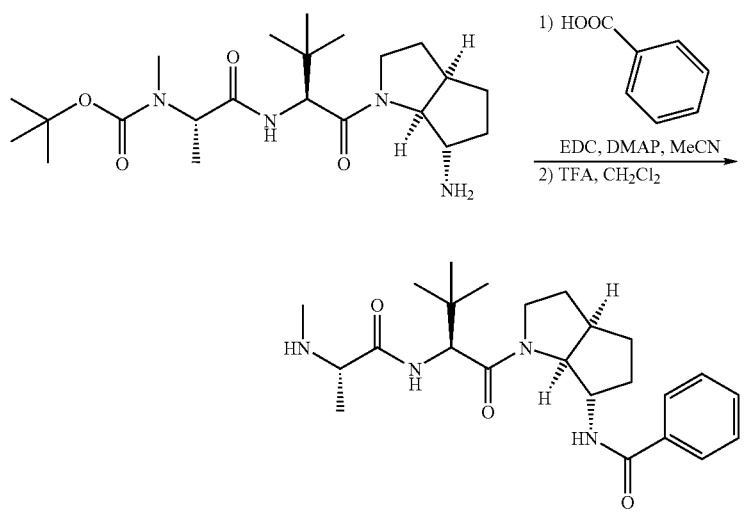

The Boc-protected amine intermediate prepared according to the procedures of example 3 was coupled with commercially available benzoic acid under typical EDC coupling conditions followed by Boc group removal and HPLC purification to yield the final compound (16%).

Example 12

Compound 11

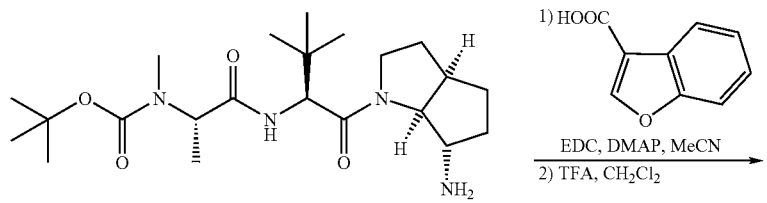

-continued

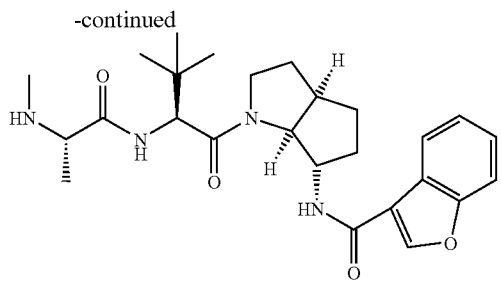

The Boc-protected amine intermediate prepared according to the procedures of example 3 was coupled with commercially available benzofuran-3-carboxylic acid under typical EDC coupling conditions followed by Boc group removal and HPLC purification to yield the final compound (32%).

Example 13

Compound 21

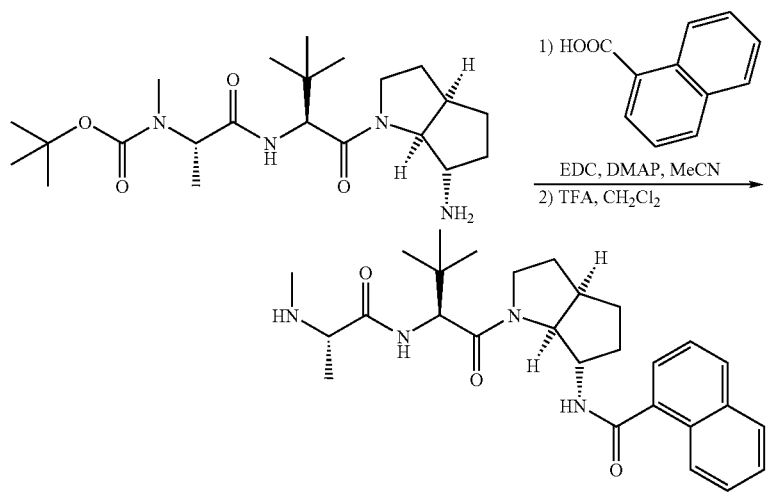

The Boc-protected amine intermediate prepared according to the procedures of example 3 was coupled with commercially available naphthalene-l-carboxylic acid under typical EDC coupling conditions followed by Boc group removal and HPLC purification to yield the final compound (28%).

Example 14

Compound 24

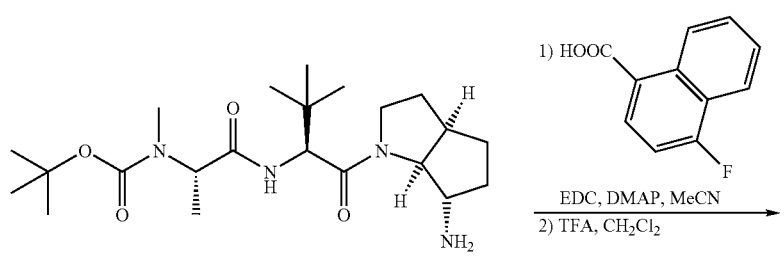

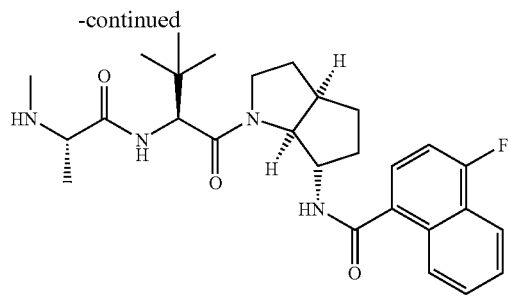

The Boc-protected amine intermediate prepared according to the procedures of example 3 was coupled with commercially available 4-fluoro-naphthalene-1-carboxylic acid under typical EDC coupling conditions followed by Boc group removal and HPLC purification to yield the final compound (33%).

Example 15

Compound 6

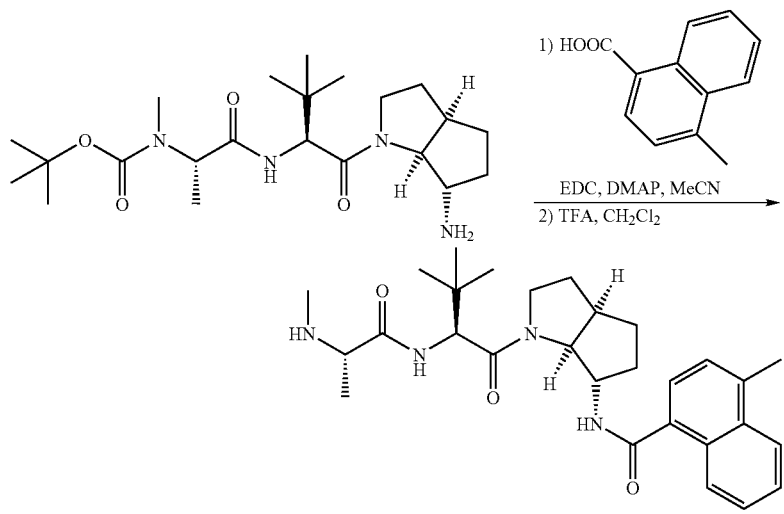

The Boc-protected amine intermediate prepared according to the procedures of example 3 was coupled with commercially available 4-methyl-naphthalene-1-carboxylic acid under typical EDC coupling conditions followed by Boc group removal and HPLC purification to yield the final compound (39%).

Example 16

Compound 4

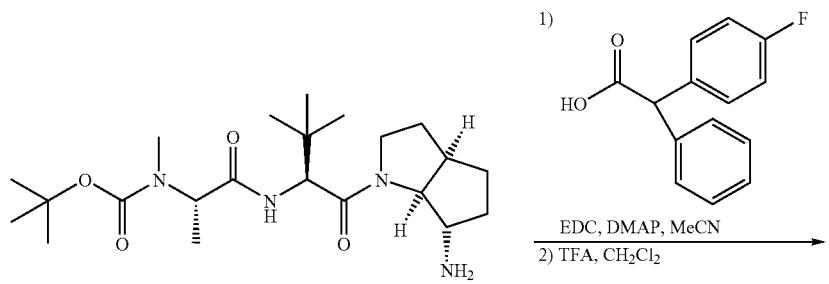

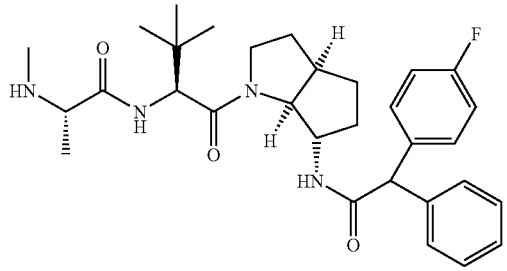

The Boc-protected amine intermediate prepared according to the procedures of example 3 was coupled with commercially available (4-Fluoro-phenyl)-phenyl-acetic acid under typical EDC coupling conditions followed by Boc group removal and HPLC purification to yield the final compound (68%).

Example 17

Compound 3

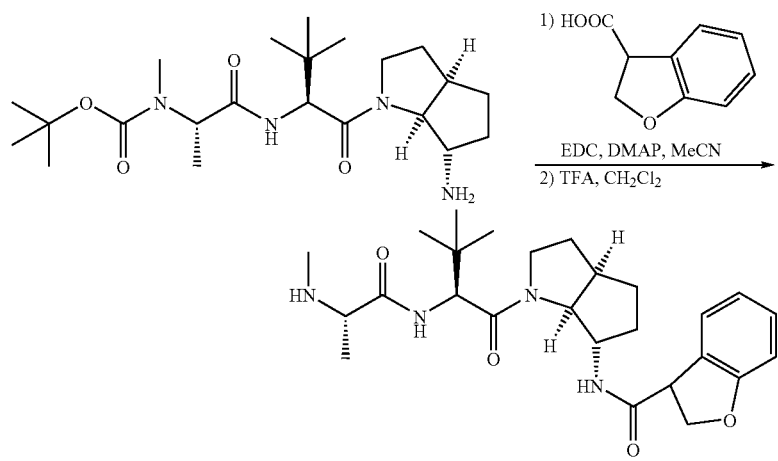

The Boc-protected amine intermediate prepared according to the procedures of example 3 was coupled with commercially available 2,3-dihydro-benzofuran-3-carboxylic acid under typical EDC coupling conditions followed by Boc group removal and HPLC purification to yield the final compound (39%).

Example 18

Compound 12

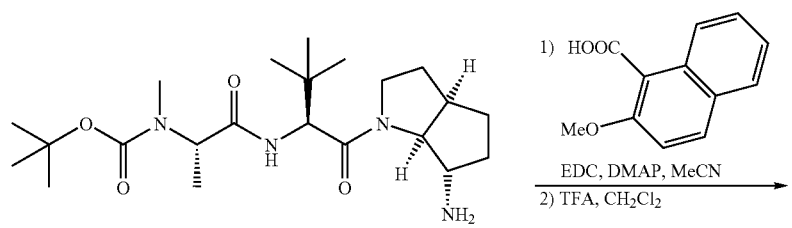

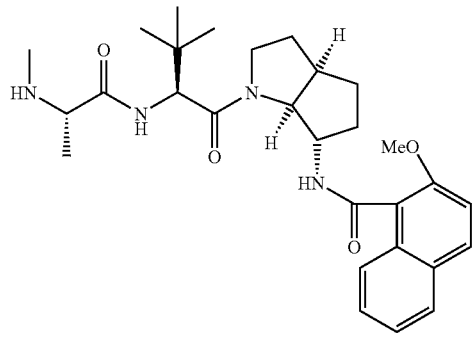

The Boc-protected amine intermediate prepared according to the procedures of example 3 was coupled with commercially available 2-methoxy-naphthalene-1-carboxylic acid under typical EDC coupling conditions followed by Boc group removal and HPLC purification to yield the final compound (52%).

Example 19

Compound 28

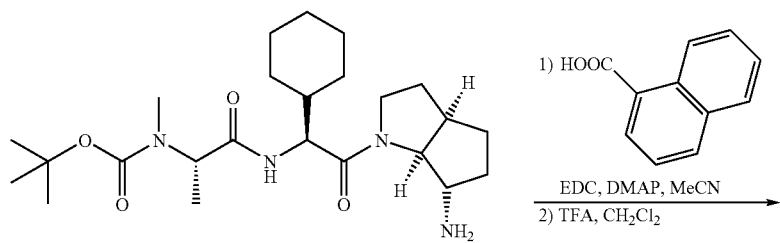

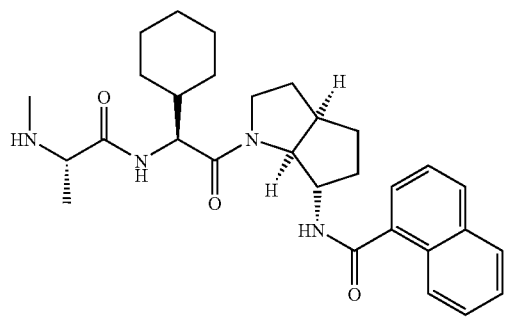

The Boc-protected amine intermediate prepared according to the procedures of example 3 was coupled with commercially available naphthalene-1-carboxylic acid under typical EDC coupling conditions followed by Boc group removal and HPLC purification to yield the final compound (41%).

Example 20

Compound 25

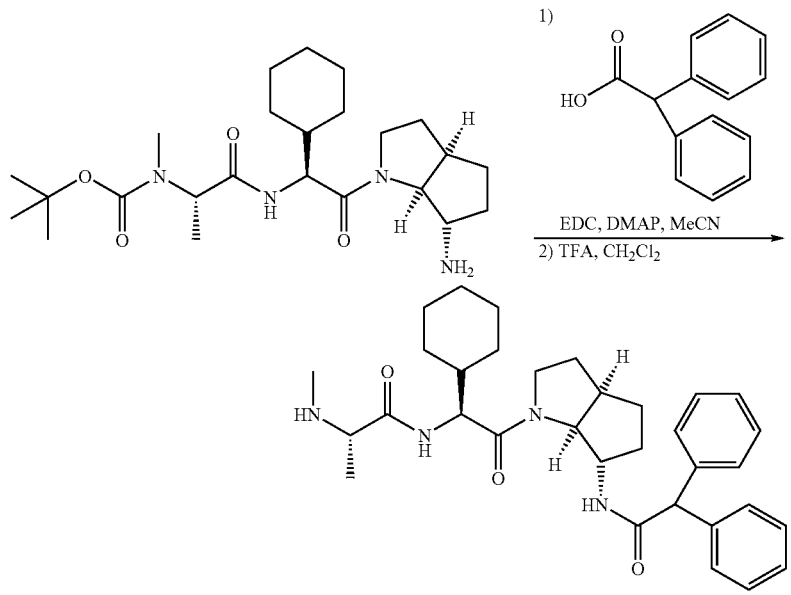

The Boc-protected amine intermediate prepared according to the procedures of example 3 was coupled with commercially available diphenyl-acetic acid under typical EDC coupling conditions followed by Boc group removal and HPLC purification to yield the final compound (33%).

Example 21

Compound 27

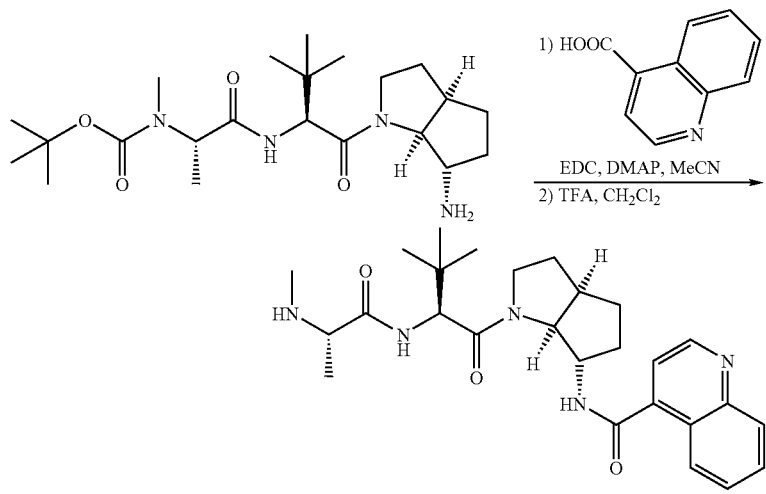

The Boc-protected amine intermediate prepared according to the procedures of example 3 was coupled with commercially available quinoline-4-carboxylic acid under typical EDC coupling conditions followed by Boc group removal and HPLC purification to yield the final compound (78%).

Example 22

Compound 26

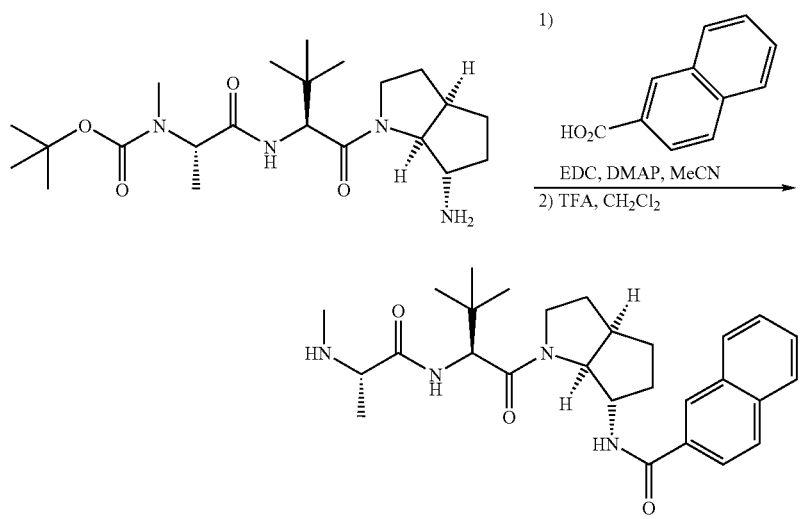

The Boc-protected amine intermediate prepared according to the procedures of example 3 was coupled with commercially available naphthalene-2-carboxylic acid under typical EDC coupling conditions followed by Boc group removal and HPLC purification to yield the final compound (79%).

Example 23

Compound 16

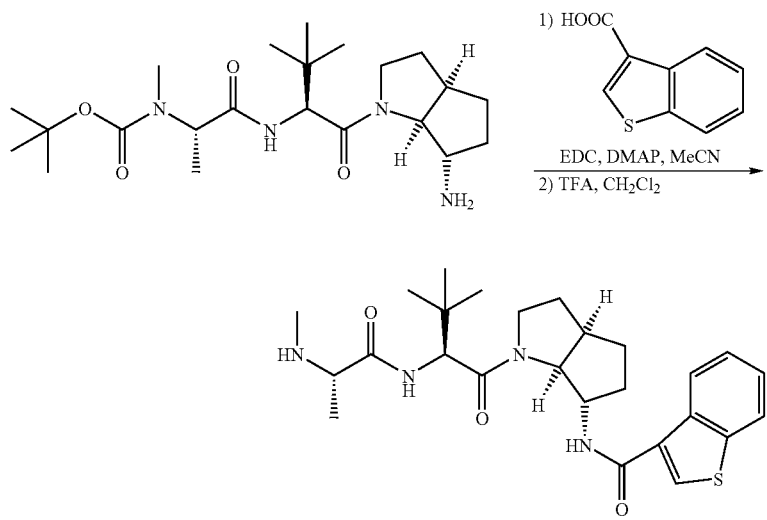

The Boc-protected amine intermediate prepared according to the procedures of example 3 was coupled with commercially available benzo[b]thiophene-3-carboxylic acid under typical EDC coupling conditions followed by Boc group removal and HPLC purification to yield the final compound (49%).

Example 24

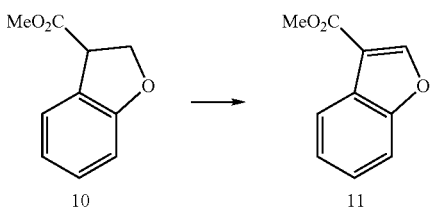

A mixture of dihydrobezofuran 10 (160 mg, 0.9 mmol) DDQ (300 mg) and $CH_2Cl_2$ (11 mL) was maintained at room temp. for 2 days. The solution was diluted with 50% ethyl acetate-hexanes and washed with 0.5N NaOH (3×10 mL), brine (1×10 mL), dried ($Na_2SO_4$), filtered, and concentrated to afford 150 mg of benzofuran methyl ester 11.

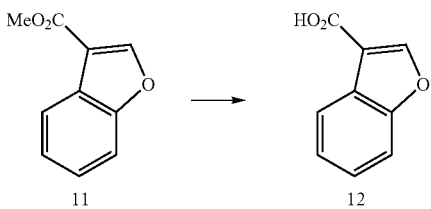

A mixture of ester 11 (150 mg) $LiOH.H_2O$ (95 mg) THF (5 mL) and water (2.5 mL) was stirred vigorously for 2 days. The reaction was quenched with sat. aq. $NH_4Cl$ (10 mL) and the THF removed under reduced pressure. The aq phase was extracted with $CH_2Cl_2$ (1×50 mL), dried ($Na_2SO_4$), filtered, and concentrated to afford 140 mg of benzofuran 12.

Example 25

IAP Inhibition Assays

In the following experiments was used a chimeric BIR domain referred to as MLXBIR3SG in which 11 of 110 residues correspond to those found in XIAP-BIR3, while the remainder correspond to ML-IAP-BIR. The chimeric protein MLXBIR3SG was shown to bind and inhibit caspase-9 significantly better than either of the native BIR domains, but bound Smac-based peptides and mature Smac with affinities similar to those of native ML-IAP-BIR. The improved caspase-9 inhibition of the chimeric BIR domain MLXBIR3SG has been correlated with increased inhibition of doxorubicin-induced apoptosis when transfected into MCF7 cells.

```
MLXBIR3SG sequence:                      (SEQ ID NO.: 1)
MGSSHHHHHHSSGLVPRGSHMLETEEEEEGAGATLSRGPAFPGMGSEEL

RLASFYDWPLTAEVPPELLAAAGFFHTGHQDKVRCFFCYGGLQSWKRGDD

PWTEHAKWFPGCQFLLRSKGQEYINNIHLTHSL
```

TR-FRET Peptide Binding Assay

Time-Resolved Fluorescence Resonance Energy Transfer competition experiments were performed on the Wallac Victor2 Multilabeled Counter Reader (Perkin Elmer Life and Analytical Sciences, Inc.) according to the procedures of Kolb et al (Journal of Biomolecular Screening, 1996, 1(4): 203). A reagent cocktail containing 300 nM his-tagged MLXBIR3SG; 200 nM biotinylated SMAC peptide (AVPI); 5 µg/mL anti-his allophycocyanin (XL665) (CISBio International); and 200 ng/mL streptavidin-europium (Perkin Elmer) was prepared in reagent buffer (50 mM Tris [pH 7.2], 120 mM NaCl, 0.1% bovine globulins, 5 mM DTT and 0.05% octylglucoside). (Alternatively, this cocktail can be made using europium-labeled anti-His (Perkin Elmer) and streptavidin-allophycocyanin (Perkin Elmer) at concentrations of 6.5 nM and 25 nM, respectively). The reagent cocktail was incubated at room temperature for 30 minutes. After incubation, the cocktail was added to 1:3 serial dilutions of an antagonist compound (starting concentration of 50 µM) in 384-well black FIA plates (Greiner Bio-One, Inc.). After a 90 minute incubation at room temperature, the fluorescence was read with filters for the excitation of europium (340 nm) and for the emission wavelengths of europium (615 nm) and a allophycocyanin (665 nm). Antagonist data were calculated as a ratio of the emission signal of allophycocyanin at 665 nm to that of the emission of europium at 615 nm (these ratios were multiplied by a factor of 10,000 for ease of data manipulation). The resulting values were plotted as a function of antagonist concentration and fit to a 4-parameter equation using Kaleidograph software (Synergy Software, Reading, Pa.). Indications of antagonist potency were determined from the IC50 values. Compounds of formula I' tested in this assay exhibited IC50 values of less than 200 µM indicating IAP inhibitory activity.

| compound | $IC_{50}$ (µM) |
|---|---|
| 3 | <10 |
| 4 | <10 |
| 5 | <10 |
| 6 | <10 |
| 9 | <10 |
| 11 | <10 |
| 12 | <10 |
| 13 | <10 |
| 14 | <10 |
| 16 | <10 |
| 21 | <10 |
| 22 | <10 |
| 24 | <10 |
| 25 | <10 |
| 28 | <10 |
| 42 | <10 |

Fluorescence Polarization Peptide Binding Assay

Polarization experiments were performed on an Analyst HT 96-384 (Molecular Devices Corp.) according to the procedure of Keating, S. M., Marsters, J, Beresini, M., Ladner, C., Zioncheck, K., Clark, K., Arellano, F., and Bodary., S.(2000) in *Proceedings of SPIE : In Vitro Diagnostic Instrumentation* (Cohn, G. E., Ed.) pp 128-137, Bellingham, Wash. Samples for fluorescence polarization affinity measurements were prepared by addition of 1:2 serial dilutions starting at a final concentration of 5 µM of MLXBIR3SG in polarization buffer (50 mM Tris [pH 7.2], 120 mM NaCl, 1% bovine globulins 5 mM DTT and 0.05% octylglucoside) to 5-carboxyflourescein-conjugated AVPdi-Phe-$NH_2$ (AVP-diPhe-FAM) at 5 nM final concentration.

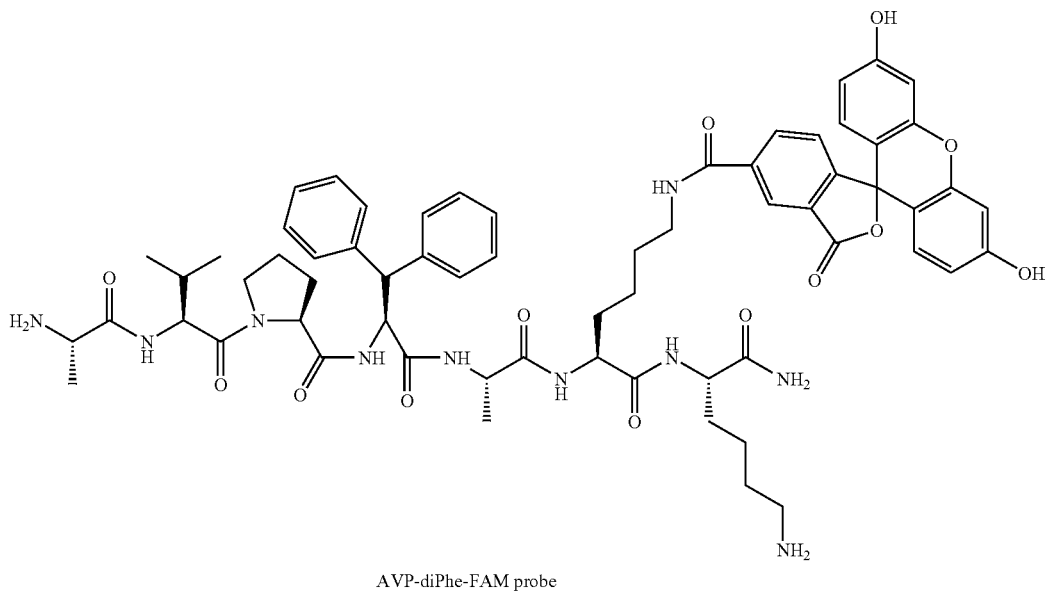

AVP-diPhe-FAM probe

The reactions were read after an incubation time of 10 minutes at room temperature with standard cut-off filters for the fluorescein fluorophore ($\lambda_{ex}$=485 nm; $\lambda_{em}$=530 nm) in 96-well black HE96 plates (Molecular Devices Corp.). Fluorescence values were plotted as a function of the protein concentration, and the IC50s were obtained by fitting the data to a 4-parameter equation using Kaleidograph software (Synergy software, Reading, Pa.). Competition experiments were performed by addition of the MLXBIR3SG at 30 nM to wells containing 5 nM of the AVP-diPhe-FAM probe as well as 1:3 serial dilutions of antagonist compounds starting at a concentration of 300 µM in the polarization buffer. Samples were read after a 10-minute incubation. Fluorescence polarization values were plotted as a function of the antagonist concentration, and the $IC_{50}$ values were obtained by fitting the data to a 4-parameter equation using Kaleidograph software (Synergy software, Reading, Pa.). Inhibition constants ($K_i$) for the antagonists were determined from the $IC_{50}$ values.

| compound | $IC_{50}$ (µM) | $K_i$ (µM) |
| --- | --- | --- |
| 4 | <1 | <0.2 |
| 6 | <1 | <0.2 |
| 12 | <1 | <0.2 |
| 16 | <1 | <0.2 |
| 24 | <1 | <0.2 |

We claim:

1. A compound of formula I:

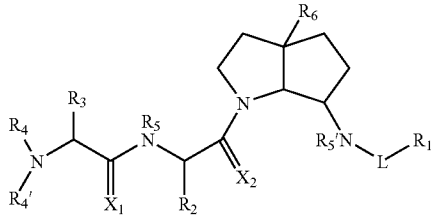

wherein $X_1$ and $X_2$ are independently O or S;

L is a bond, —C($X_3$)—, —C($X_3$)N$R_{12}$ or —C($X_3$)O— wherein $X_3$ is O or S and $R_{12}$ is H or $R_1$;

$R_1$ is alkyl, a carbocycle, carbocycle-substituted alkyl, a heterocycle or heterocycle-substituted alkyl, wherein each is optionally substituted with halogen, hydroxyl, mercapto, carboxyl, alkyl, haloalkyl, alkoxy, alkylsulfonyl, amino, nitro, aryl and heteroaryl;

$R_2$ is alkyl, cycloalkyl, cycloalkylalkyl, aryl, aralkyl, a heterocycle or heterocyclylalkyl;

$R_3$ is H or alkyl;

$R_4$ and $R_4'$ are independently H, alkyl, aryl, aralkyl, cycloalkyl, cycloalkylalkyl, heteroaryl, or heteroaralkyl wherein each is optionally substituted with halogen, hydroxyl, mercapto, carboxyl, alkyl, alkoxy, amino and nitro;

$R_5$, and $R_{5'}$ are each independently H or alkyl;

$R_6$ is H or alkyl;

and salts and solvates thereof.

2. The compound of claim 1, wherein $R_3$ is methyl.

3. The compound of claim 2, wherein L is —C($X_3$)— and $R_1$ is selected from the group consisting of IIa-IId:

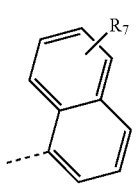

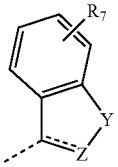

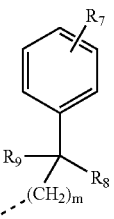

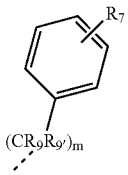

wherein $R_7$ is H, alkyl, alkoxy, halogen, hydroxyl, mercapto, carboxyl, amino, nitro, aryl, aryloxy, aralkyl, cycloalkyl, cycloalkylalkyl, heteroaryl, or heteroaralkyl;

$R_8$ is H, alkyl, aryl or heteroaryl optionally substituted with halogen, hydroxyl, alkoxy, carboxyl, or amino;

$R_9$ and $R_{9'}$ are independently H or alkyl;

Y is NH, N$R_{10}$, O or S wherein $R_{10}$ is H, alkyl or aryl;

Z is CH, $CH_2$ or N; and m is 0, 1, 2 or 3.

4. The compound of claim 3, wherein $R_1$ is the group of formula IIa.

5. The compound of claim 4, wherein $R_7$ is H, halogen, alkyl, hydroxyl or alkoxy.

6. The compound of claim 4, wherein $R_2$ is alkyl or cycloalkyl.

7. The compound of claim 4, wherein $R_2$ is isopropyl, t-butyl, or cyclohexyl.

8. The compound of claim 4, wherein $R_3$ is methyl.

9. The compound of claim 4, wherein $R_4$ is H or methyl, and $R_{4'}$ is H.

10. The compound of claim 4, wherein $X_1$, $X_2$ and $X_3$ are O and $R_5$, $R_{5'}$ and $R_6$ are each H.

11. The compound of claim 3, wherein $R_1$ is the group of formula IIb.

12. The compound of claim 11, wherein the group of formula IIb is benzothiophene, indole, N-methyl indole, benzofuran or 2,3-dihydro-benzofuran.

13. The compound of claim 11, wherein $R_2$ is alkyl or cycloalkyl.

14. The compound of claim 11, wherein $R_2$ is isopropyl, t-butyl, or cyclohexyl.

15. The compound of claim 11, wherein $R_3$ is methyl.

16. The compound of claim 11, wherein $R_4$ is H or methyl, and $R_{4'}$ is H.

17. The compound of claim 11, wherein $X_1$, $X_2$ and $X_3$ are O and $R_5$, $R_{5'}$ and $R_6$ are each H.

18. The compound of claim 3, wherein $R_1$ is the group of formula IIc.

19. The compound of claim 18, wherein $R_1$ is the group of the formula IIc$^1$:

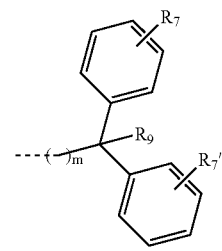

IIc' wherein
$R_7$ and $R_{7'}$ are each independently H, alkyl, alkoxy, halogen, hydroxyl, mercapto, carboxyl, amino, nitro, aryl, aryloxy, aralkyl, cycloalkyl, cycloalkylalkyl, heteroaryl, or heteroaralkyl;
$R_9$ is H or alkyl; and
m is 0 or 1.

20. The compound of claim 18, wherein $R_7$ is H, $R_9$ is H and m is 0.

* * * * *